United States Patent [19]
Rosenberg et al.

[11] Patent Number: 5,593,974
[45] Date of Patent: Jan. 14, 1997

[54] LOCALIZED OLIGONUCLEOTIDE THERAPY

[75] Inventors: Robert D. Rosenberg, Jamestown, R.I.; Michael Simons, Chestnut Hill, Mass.; Elazer Edelman, Brookline, Mass.; Robert S. Langer, Newton, Mass.; Jean-Luc DeKeyser, Brussels, Belgium

[73] Assignee: Massachusetts Institute of Technology, Cambridge, Mass.

[21] Appl. No.: 369,282

[22] Filed: Jan. 6, 1995

Related U.S. Application Data

[63] Continuation of Ser. No. 855,416, Mar. 18, 1992, abandoned, which is a continuation-in-part of Ser. No. 792,146, Nov. 8, 1991, which is a continuation-in-part of Ser. No. 723,454, Jun. 28, 1991, abandoned.

[51] Int. Cl.$^6$ .................................. A61K 48/00
[52] U.S. Cl. ..................... 514/44; 424/426; 424/486; 536/24.5; 604/52; 604/53; 935/44; 935/52
[58] Field of Search ............................... 514/44; 424/423, 424/428, 426, 486; 536/24.5; 604/52, 53, 890.1; 935/44, 52

[56] References Cited

U.S. PATENT DOCUMENTS

| | | | |
|---|---|---|---|
| 3,797,485 | 3/1974 | Urquhart | 604/93 |
| 4,806,463 | 2/1989 | Goodchild et al. | 435/5 |
| 4,898,732 | 2/1990 | Fernandez | 424/422 |
| 5,098,890 | 3/1992 | Gewirtz et al. | 514/44 |
| 5,171,217 | 12/1992 | March et al. | 604/53 |

FOREIGN PATENT DOCUMENTS

| | | |
|---|---|---|
| 1072413 | 2/1980 | Canada. |
| 0248531 | 12/1987 | European Pat. Off. . |
| 0326727 | 8/1989 | European Pat. Off. . |
| 0417572 | 3/1991 | European Pat. Off. . |
| 9001969 | 3/1990 | WIPO . |
| 9005445 | 5/1990 | WIPO . |
| 9117266 | 11/1991 | WIPO . |

OTHER PUBLICATIONS

CF Bennett (1996) Science 271:434.
K. Morikawa et al (1987) Cancer Research 47:37–41.
P Westermann et al (1989) Biomed Biochem Acta 48:85–93.
CA Stein et al (1993) Science 261:1004–1012.
RWeiss (1991) Science News 139:108–109.
Bennett et al (1994) J Clin Investigation 93:820–828.
Abe et al (1994) Biochem Biophys Res Commun. 198:16–24.
Anderson (1992) Cardiovasc. Pathol. 1:263–278.
EG Nabel et al (1990) Science 249:1285–1288.
Agrawal et. al. 1988, PNAS 85:7079–7083.
Jaskulski et al. 1988, Science 240:1544–1546.
Woolf et. al. 1990, NAR 18(7):1763–1769.
Sourin et al. 1988, PNAS 85: 7448–7451.
Applied Biosystems, User Bulletin No. 49, 1988.
JF Milligan et al (1993) J Med. Chem 36:1923–1937.
Dilley et al., Atherosciersosis, 63 (1987) pp. 99–107.
Libby et al., PDGF and Human Atheroma, 118 No. 23 (1988) pp. 1493–1498.
Schwartz et al., Cir Res 58:427–444, 1986.
Kuro et al., Jour. Bio Chem. vol. 264, No. 31 (1989) 18727–18275.
Clowes et al., Jour. Cell Bio. 107:1939–1945 (1988).
Nobuyoshi et al., JACC vol. 17, No. 2. 433—439 (1991).
Dilley et al., Arch Surg. vol. 123:691–696 (1988).

(List continued on next page.)

*Primary Examiner*—Bruce R. Campell

[57] ABSTRACT

Disclosed is a method for localized application of antisense oligonucleotides, which has been found to be effective in inhibiting expression and translation of a variety of genes. The method utilizes antisense oligonucleotides which are specific for the mRNA transcribed from the gene of interest. The antisense oligonucleotides are applied directly to the desired locus of the cells to be treated, where they hybridize with the mRNA and inhibit expression of the gene. Devices for localized antisense application and methods for making them also are described.

20 Claims, 11 Drawing Sheets

OTHER PUBLICATIONS

Schwartz et al., Hum Pathol 18:240–247 (1987).
Thompson et al., Nature 319:374–380 (1986).
Luscher et al., Genes & Development 4:2235–2241 (1990).
Reilly et al., Jour. Cell. Phys. 131:149–157 (1987).
Nature 265:625–626 (1977).
Guyton et al., Cir. Res. 46:625–634 (1980).
Fritze et al., Jour. Cell Bio. 100:1041–1049 (1985).
Katsuragawa et al., Inst. Basic Med Sci. 610–616.
Kawamoto et al., Jour. Cell Bio. 112:915–924 (1991).
Kawamoto et al., Jour. Bio. Chem. 262:7282–7288 (1987).
Fager et al., In Vitro Cell. Devel. Bio. 25:511–520 (1989).
Weir et al., Supp. Cir. 82:1990 574.
Shohet et al., Proc. Natl. Acad. Sci. 86:7726–7730 (1989).
Reilly Jour. Cell. Phys. 142:342–351.
Klein et al., Prog. Card. Dis.32:365–382 (1990).
C. F. Reilly et al., J. Biol. Chem. 264(12) 6990–6995 (1989).
T. J. Gonda et al., The EMBO Journal, 4(8) 2003–2008 (1985).
M. Simons et al., Cir. Res., 69(2): 530–539 (1991).
G. Anfossi et al., Proc. Nat'l Acad. Sci USA, 86: 3379–3383 (1989).

Brown et al., "Expression of the C–myb Proto–oncogene in Bovine Vascular Smooth Muscle Cells," *J. Biol. Chem.*, 267:4625–30 (1992).

Pickering et al., "Proliferation of Human Vascular Smooth Muscle Cells Using Antisense Oligonucleotides to PCNA," *J. Am. Coll. Cardiol.*, 19:165A (1992).

Rothenberg et al., "Oligodeoxynucleotides as Anti–Sense Inhibitors of Gene Expression: Therapeutic Implications," *J. National Cancer Institute*, 81:1539–1545 (1989).

Saez et al., "Human Nonmuscle Myosin Heavy Chain mRNA: Generation of Diversity Through Alternative Polyadenylation," *PNAS*, 87:1164–1168 (1990).

Shaw et al., "Modified Deoxyoligonucleotides Stable to Exonuclease Degradaton in Serum," *Nucleic Acids Research*, 19:747–750 (1991).

Simons et al., "Antisense Nomuscle Myosin Heavy Chain and c–MYB Oligonucleotides Suppress Smoth Muscle Cell Proliferation in Vitro," *Circulation Research*, 70:835–843 (1992).

Uhlmann et al., "Antisense Oligonucleotides: A New Therapeutic Principal," *Chemical Reviews*, 90:543–584 (1990).

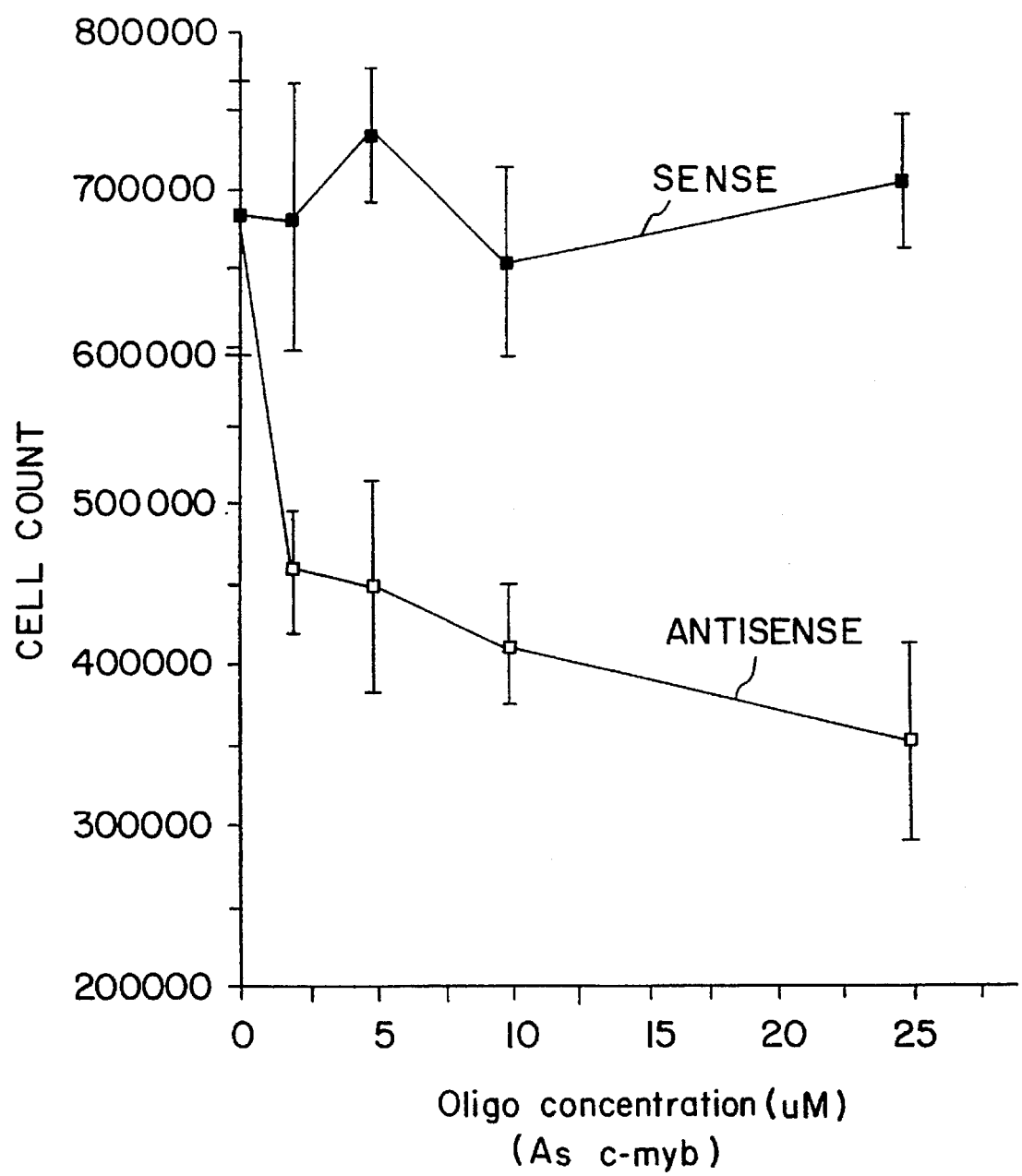

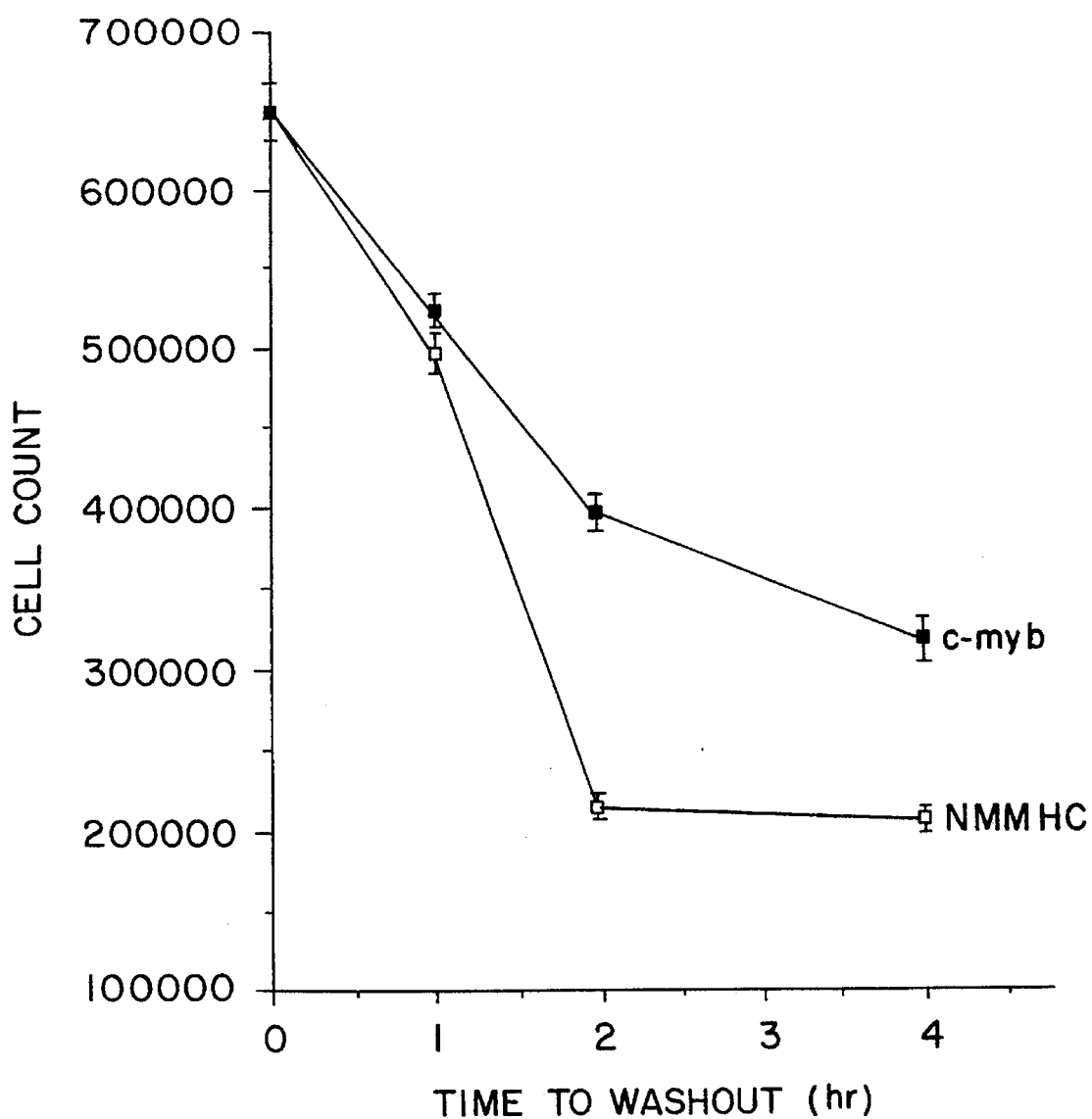

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: cDNA ( i v ) ANTI-SENSE: YES ( i x ) FEATURE:
      ( A ) NAME/KEY: misc_feature
      ( B ) LOCATION: 1..18

( D ) OTHER INFORMATION: /standard_name= "ANTISENSE MOUSE
                            C-MYB"
                            / note= "ANTISENSE SEQUENCE TO MOUSE C-MYB"

( x i ) SEQUENCE DESCRIPTION: SEQ ID NO:1:

GTGTCGGGGT CTCCGGGC                                                                                        18

( 2 ) INFORMATION FOR SEQ ID NO:2:

( i ) SEQUENCE CHARACTERISTICS:
                    ( A ) LENGTH: 18 base pairs
                    ( B ) TYPE: nucleic acid
                    ( C ) STRANDEDNESS: single
                    ( D ) TOPOLOGY: linear ( i i ) MOLECULE TYPE: cDNA ( i v ) ANTI-SENSE: YES ( i x ) FEATURE:
                    ( A ) NAME/KEY: misc_feature
                    ( B ) LOCATION: 1..18
                    ( D ) OTHER INFORMATION: /standard_name= "ANTISENSE HUMAN
                            NMMHC"
                            / note= "ANTISENSE SEQUENCE TO HUMAN NMMHC"

( x i ) SEQUENCE DESCRIPTION: SEQ ID NO:2:

CATGTCCTCC ACCTTGGA                                                                                        18

( 2 ) INFORMATION FOR SEQ ID NO:3:

( i ) SEQUENCE CHARACTERISTICS:
                    ( A ) LENGTH: 21 base pairs
                    ( B ) TYPE: nucleic acid
                    ( C ) STRANDEDNESS: single
                    ( D ) TOPOLOGY: linear ( i i ) MOLECULE TYPE: cDNA ( i v ) ANTI-SENSE: YES ( i x ) FEATURE:
                    ( A ) NAME/KEY: misc_feature
                    ( B ) LOCATION: 1..21
                    ( D ) OTHER INFORMATION: /standard_name= "ANTISENSE MOUSE
                            THROMBOMODULIN"
                            / note= "ANTISENSE SEQUENCE TO MOUSE
                            THROMBOMODULIN"

( x i ) SEQUENCE DESCRIPTION: SEQ ID NO:3:

ACCCAGAAAG AAAATCCCAA G                                                                                    21

( 2 ) INFORMATION FOR SEQ ID NO:4:

( i ) SEQUENCE CHARACTERISTICS:
                    ( A ) LENGTH: 18 base pairs
                    ( B ) TYPE: nucleic acid
                    ( C ) STRANDEDNESS: single
                    ( D ) TOPOLOGY: linear ( i i ) MOLECULE TYPE: cDNA ( i v ) ANTI-SENSE: YES ( i x ) FEATURE:
                    ( A ) NAME/KEY: misc_feature
                    ( B ) LOCATION: 1..18
                    ( D ) OTHER INFORMATION: /standard_name= "ANTISENSE HUMAN
                            C-MYB"
                            / note= "ANTISENSE SEQUENCE TO HUMAN C-MYB"

( x i ) SEQUENCE DESCRIPTION: SEQ ID NO:4:

GTGCCGGGGT CTTCGGGC                                                                                        18

(2) INFORMATION FOR SEQ ID NO:5:

(i) SEQUENCE CHARACTERISTICS:
  (A) LENGTH: 18 base pairs
  (B) TYPE: nucleic acid
  (C) STRANDEDNESS: single
  (D) TOPOLOGY: linear (ii) MOLECULE TYPE: cDNA (iv) ANTI-SENSE: YES (ix) FEATURE:
  (A) NAME/KEY: misc_feature
  (B) LOCATION: 1..18
  (D) OTHER INFORMATION: /standard_name= "ANTISENSE PCNA"
   / note= "ANTISENSE SEQUENCE TO PCNA"

(xi) SEQUENCE DESCRIPTION: SEQ ID NO:5:

GATCAGGCGT GCCTCAAA                               18

LOCALIZED OLIGONUCLEOTIDE THERAPY

GOVERNMENT INTEREST

The United States government has certain rights in this invention by virtue of grant numbers NIH-2-POI-HL-33014 and NIH-P01-HL-41484.

RELATED APPLICATIONS

This is a continuation of application Ser. No. 07/855,416 filed on Mar. 18, 1992, abandoned, which is a continuation-in-part of applications U.S. Ser. No. 07/792,146 entitled "Localized Oligonucleotide Therapy" filed Nov. 8, 1991; which is a continuation-in-part of U.S. Ser. No. 07/723,454, abandoned, entitled "Methods and Reagents for Inhibiting Smooth Muscle Proliferation" filed Jun. 28, 1991, both by Robert D. Rosenberg et al., the entire disclosures of which are hereby incorporated herein by reference.

BACKGROUND OF THE INVENTION

This invention relates to a method of delivery of antisense oligonucleotide to a preselected locus in vivo, useful in the treatment of disease.

In the last several years, it has been demonstrated that oligonucleotides are capable of inhibiting the replication of certain viruses in tissue culture systems. For example, Zamecnik and Stephenson, *Proc. Natl. Acad. Sci. U.S.A.*, 75:280–284 (1978), showed oligonucleotide-mediated inhibition of virus replication in tissue culture, using Rous Sarcoma Virus. Zamecnik et al., *Proc. Natl. Acad. Sci. U.S.A.*,83:4145–4146 (1986), demonstrated inhibition in tissue culture of the HTLV-III virus (now HIV-1) which is the etiological agent of AIDS. Oligonucleotides also have been used to suppress expression of selected non-viral genes by blocking translation of the protein encoded by the genes. Goodchild, et al., *Arch. Biochem. Biophys.*,264:401–409 (1988) report that rabbit-globin synthesis can be inhibited by oligonucleotides in a cell-free system. Treatment with antisense c-myb has been shown to block proliferation of human myeloid leukemic cell lines in vitro. G. Anfossi, et al., *Proc. Natl. Acad. Sci. USA*, 86:3379 (1989).

A drawback to this method is that oligonucleotides are subject to being degraded or inactivated by cellular endogenous nucleases. To counter this problem, some researchers have used modified oligonucleotides, e.g., having altered internucleotide linkages, in which the naturally occurring phosphodiester linkages have been replaced with another linkage. For example, Agrawal et al., *Proc Natl. Acad. Sci. U.S.A.*,85:7079–7083 (1988) showed increased inhibition in tissue culture of HIV-1 using oligonucleotide phosphoramidates and phosphorothioates. Sarin et al., *Proc. Natl. Acad, Sci. U.S.A.*,85:7448–7451 (1988) demonstrated increased inhibition of HIV-1 using oligonucleotide methylphosphonates. Agrawal et al., *Proc. Natl. Acad. Sci. U.S.A.*, 86:7790–7794 (1989) showed inhibition of HIV-1 replication in both early-infected and chronically infected cell cultures, using nucleotide sequence-specific oligonucleotide phosphorothioates. Leither et al., *Proc. Natl. Acad. Sci. U.S.A.*,87:3430–3434 (1990) report inhibition in tissue culture of influenza virus replication by oligonucleotide phosphorothioates.

Oligonucleotides having artificial linkages have been shown to be resistant to degradation in vivo. For example, Shaw et al., in *Nucleic Acids Res.*,19:747–750 (1991), report that otherwise unmodified oligonucleotides become more resistant to nucleases in vivo when they are blocked at the 3' end by certain capping structures and that uncapped oligonucleotide phosphorothioates are not degraded in vivo.

While antisense oligonucleotides have been shown to be capable of interfering selectively with protein synthesis, and significant progress has been made on improving their intracellular stability, the problem remains that oligonucleotides must reach their intended intracellular site of action in the body in order to be effective. Where the intended therapeutic effect is a systemic one, oligonucleotides may be administered systemically. However, when it is necessary or desirable to administer the oligonucleotide to a specific region within the body, systemic administration typically will be unsatisfactory. This is especially true when the target mRNA is present in normal cells as well as in the target tissue, and when antisense mRNA binding in normal cells induces unwanted physiological effects. Stated differently, the dosage of antisense oligonucleotide administered systemically that is sufficient to have the desired effect locally may be toxic to the patient.

An example of a treatment strategy which could greatly benefit from development of a method of limiting the effect of antisense oligonucleotide to a target tissue is the inhibition of smooth muscle cell proliferation which leads to restenosis following vascular trauma.

Smooth muscle cell proliferation is a poorly understood process that plays a major role in a number of pathological states including atherosclerosis and hypertension. It is the leading cause of long-term failure of coronary and peripheral angioplasty as well as of coronary bypass grafts.

Vascular smooth muscle cells in adult animals display a well defined phenotype characterized by an abundance of contractile proteins, primarily smooth muscle actin and myosins, as reviewed by S. M. Schwartz, G. R. Campbell, J. H. Campbell, *Circ. Res.*, 58,427 (1986), and a distinct lack of rough endoplasmic reticulum. When subjected to injury in vivo or placed in an in vitro cell culture, adult smooth muscle cells (SMC) undergo a distinct phenotypic change and lose their "differentiated" state. The cells acquire large amounts of endoplasmic reticulum and gain actively synthesizing extracellular matrix. In addition, they begin expressing a number of new proteins including non-muscle myosins and actins, and PDGF A chain, as reported by R. J. Dilley, et al., *Atherosclerosis,* 63:99 (1987), P. Libby, et al., *N. Engl. J. Med.,* 318:1493 (1988), while the expression of smooth muscle-specific contractile proteins such as smooth muscle myosin heavy chain and alpha actin decline, as shown by M. Kuro-o, et al. *J. Biol. Chem.*, 264:18272 (1989) and A. W. Clowes, et al. *J. Cell. Biol.,* 107:1939 (1988).

A nuclear oncogene c-myb may play an important role in these changes. The oncogene is homologous to the transforming gene of the avian myeloblastosis virus. Although considered originally to be expressed only in hematopoietic cells, c-myb has been shown to be present in chick embryo fibroblasts as well as in proliferating SMCs. C. B. Thompson, et al. *Nature,* 319:374 (1986); C. F. Reilly, et al. *J. Biol Chem.,* 264:6990 (1989). The human c-myb gene has been isolated, cloned and sequenced. Majello et al., *Proc. Natl. Acad. Sci. USA,* 83:9636–9640 (1986). The expression of c-myb is growth-dependent. It is present in a low level in quiescent cells but increases rapidly as cells begin to proliferate and peaks near the late $G_1$ phase of the cell cycle. C. F. Reilly, et al. *J. Biol. Chem.,* 264:6990 (1989). Furthermore, expression of c-myb appears to correlate with the differentiation state of the cell. Myeloid erythroleukemia cells have been induced to differentiate and thereby decrease c-myb expression.

Heparin, as well as closely related heparin proteoglycans, can block smooth muscle cell proliferation in vivo as well as in vitro. A. W. Clowes, M. J. Karnovsky *Nature*, 265:625 (1977); C. R. Reilly, et al., *J. Cell Physiol.*, 129, 11 (1986); J. R. Guyton, et al., *Circ. Res.*, 46, 625 (1980); and L. M. S. Fritze, et al., *J. Cell. Biol.*, 100:1041 (1985). This block occurs in a late $G_1$ phase of the cell cycle and is associated with a decrease in the level of c-myb (but not that of c-fos or c-myc) expression, (C. F. Reilly, et al., *J. Biol. Chem.*, 264:6990 (1989)), and a partial return of expression of smooth muscle specific contractile proteins. M. Kuro-o, et al., *J. Biol. Chem.*, 264:18272 (1989) and A. W. Clowes, et al. *J. Cell. Biol.*, 107:1939 (1988). Since c-myb appears to be critically involved in the initiation of proliferation of quiescent smooth muscle cells, heparin may exert its antiproliferative action by its effect on c-myb. It is an object of the present invention to provide a method for delivery of oligonucleotides to a specific locus in vivo, and thereby to provide localized inhibition of expression of vital genes, oncogenes and genes encoding proteins involved in disease or other pathologic conditions.

SUMMARY OF THE INVENTION

The present invention relates to a method for inhibiting translation of a target nucleic acid sequence preferentially at a locus in vivo. The invention involves application directly to the target tissue through a surgical or catheterization procedure of specific oligonucleotides having a nucleotide sequence complementary to at least a portion of the target nucleic acid, i.e., antisense oligonucleotides. The oligonucleotides are antisense sequences specific for the messenger RNA (mRNA) transcribed from the gene whose expression is to be inhibited. The antisense oligonucleotides hybridize with the target mRNA thereby preventing its translation into the encoded protein. Thus, the present method prevents the protein encoded by a selected gene from being expressed. Furthermore, animal experiments have demonstrated dramatic local therapeutic effects in vivo.

The present oligonucleotides preferably are modified to render them resistant to degradation and/or extension by cellular nucleases or other enzymes present in vivo. This can be accomplished by methods known in the art, e.g., by incorporating one or more internal artificial internucleotide linkages, such as replacing the phosphate in the linkage with sulfur, and/or by blocking the 3' end of the oligonucleotide with capping structures. Oligonucleotides of the present invention are preferably between about 14 and 38 nucleotides in length, more preferably between 15 and 30 nucleotides.

The oligonucleotides are applied locally in order to suppress expression of the protein of choice in a circumscribed area. In a preferred embodiment, the antisense oligonucleotide is applied to the surface of the tissue at the locus disposed within a biocompatible matrix or carrier. The matrix or carrier can be a hydrogel material such as a poly(propylene oxide-ethylene oxide) gel, e.g., one which is liquid at or below room temperature, and is a gel at body temperature and above. In this embodiment, the oligonucleotides are mixed with the hydrogel material, and the mixture is applied to the desired location during surgery or by catheter. The oligonucleotides also can be applied in solution by liquefying the gel, i.e., by cooling, and are retained at the area of application as the gel solidifies. Other carriers which can be used include, for example, liposomes, microcapsules, erythrocytes and the like. The oligonucleotides also can be applied locally by direct injection, can be released from devices such as implanted stents or catheters, or delivered directly to the site by an infusion pump.

The methods of the present invention are useful in inhibiting the expression of protein encoding genes, as well as regulating non-encoding DNA such as regulatory sequences. Since the antisense oligonucleotides are delivered to a specific defined locus, they can be used in vivo when systemic administration is not possible. For example, systemically administered oligonucleotides may be inactivated by endonucleases rendering them ineffective before they reach their targets. Large doses of the oligonucleotide may be necessary for successful systemic treatment systemically, which may have harmful or toxic effects on the patient. The present method provides a means for treating a large number of specific disorders using oligonucleotide therapy by delivering an antisense sequence to the specific location where it is needed.

BRIEF DESCRIPTION OF THE DRAWINGS

FIGS. 1A and 1B are graphs of the cell count for SV-smooth muscle cells (SMC) cells treated with antisense NMMHC (A) and antisense c-myb (B) at various concentrations.

FIG. 3A is a graph of the effect on growth of SV-SMC cells treated for different time intervals with antisense c-myb and NMMHC.

DETAILED DESCRIPTION OF THE INVENTION

Figure 1A:
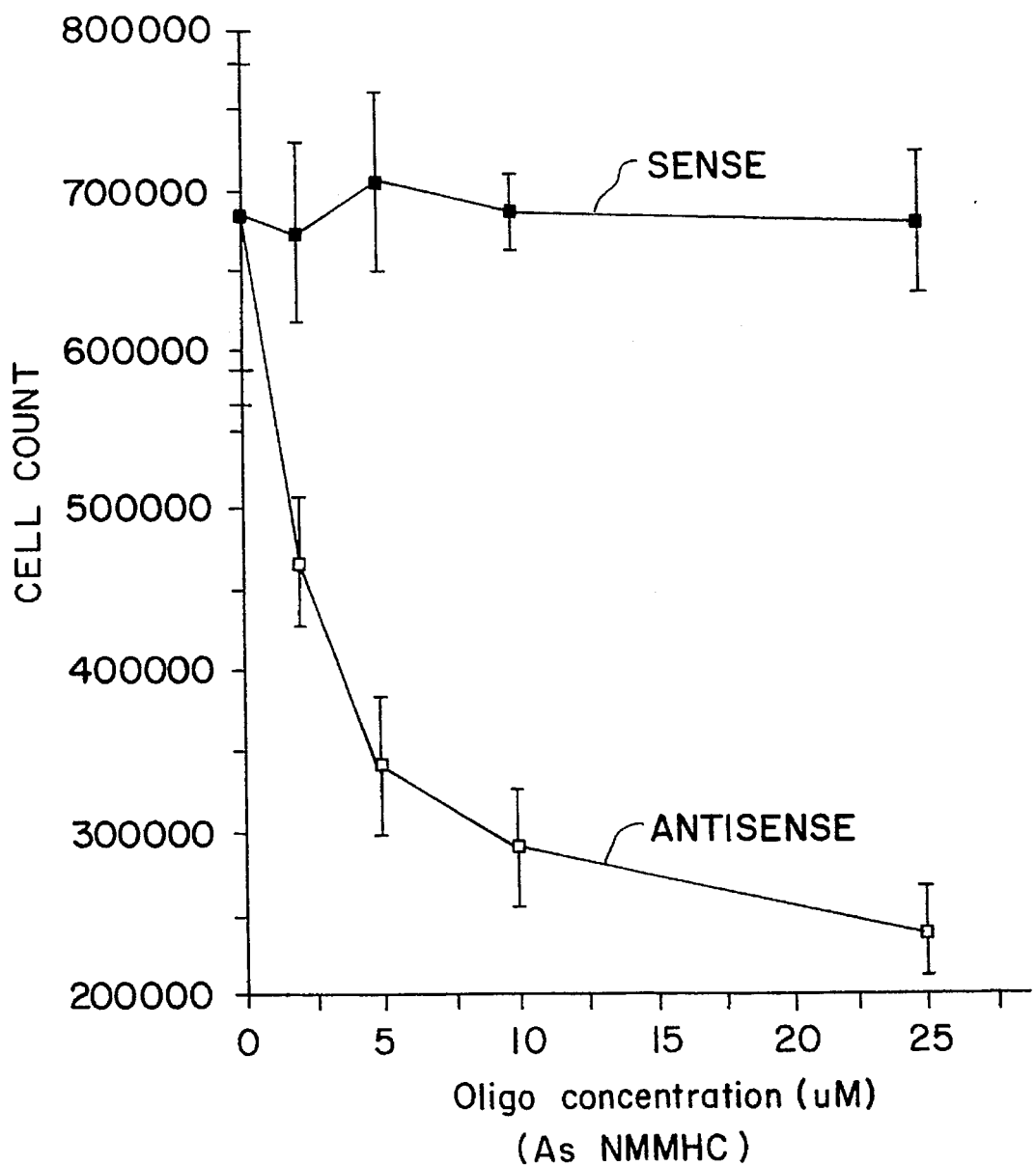

A method for inhibiting expression of protein-encoding genes using antisense oligonucleotides is described. The method is based on the localized application of the oligonucleotides to a specific site in vivo. The oligonucleotides preferably are applied directly to the target tissue in mixture with an implant or gel, or by direct injection or infusion. In one aspect, the oligonucleotides are treated to render them resistant in vivo to degradation or alteration by endogenous enzymes.

The Oligonucleotides

The therapeutic approach using antisense oligonucleotides is based on the principle that the function of a gene can be disrupted by preventing translation of the protein encoded by that gene. This can be accomplished by providing an appropriate length oligonucleotide which is complementary to at least a portion of the messenger RNA (mRNA) transcribed from the gene. The antisense strand hybridizes with the mRNA and targets the mRNA for destruction thereby preventing ribosomal translation, and subsequent protein synthesis.

The specificity of antisense oligonucleotides arises from the formation of Watson-Crick base pairing between the heterocyclic bases of the oligonucleotide and complementary bases on the target nucleic acid. For example, a nucleotide sequence sixteen nucleotides in length will be expected to occur randomly at about every $4^{16}$, or $4 \times 10^9$ nucleotides. Accordingly, such a sequence is expected to occur only once in the human genome. In contrast, a nucleotide sequence of ten nucleotides in length would occur randomly at about every $4^{10}$ or $1 \times 10^6$ nucleotides. Such a sequence might be present thousands of times in the human genome. Consequently, oligonucleotides of greater length are more specific than oligonucleotides of lesser length and are less likely to induce toxic complications that might result from unwanted hybridization. Therefore, oligonucleotides of the present invention are preferably at least 14 nucleotide bases in length. Oligonucleotides having from about 14 to about 38 bases are preferred, most preferably from about 15 to 30 bases.

The oligonucleotide sequence is selected based on analysis of the sequence of the gene to be inhibited. The gene sequence can be determined, for example, by isolation and sequencing, or if known, through the literature. The sequence of the oligonucleotide is an "antisense" sequence, that is, having a sequence complementary to the coding strand of the molecule. Thus, the sequence of the oligonucleotide is substantially identical to at least a portion of the gene sequence, and is complementary to the mRNA sequence transcribed from the gene. The oligonucleotide therapy can be used to inhibit expression of genes from viruses or other microorganisms that are essential to infection or replication, genes encoding proteins involved in a disease process, or regulatory sequences controlling the expression of proteins involved in disease or other disorder, such as an autoimmune disorder or cardiovascular disease.

Oligonucleotides useful in the present invention can be synthesized by any art-recognized technique for nucleic acid synthesis. The oligonucleotides are preferably synthesized using an automated synthesizer such as Model 8700 automated synthesizer (Milligen-Biosearch, Burlington, Mass.), as described in detail in the Examples below, or an ABI Model 380B using H-phosphonate chemistry on controlled pore glass (CPG). A detailed description of the H-phosphonate approach to synthesizing oligonucleoside phosphorothioates is provided in Agrawal and Tang, *Tetrahedron Letters* 31:7541–7544 (1990), the teachings of which are hereby incorporated herein by reference. Syntheses of oligonucleoside methylphosphonates, phosphorodithioates, phosphoramidates, phosphate esters, bridged phosphoramidates and bridge phosphorothioates are known in the art. See, for example, Agrawal and Goodchild, *Tetrahedron Letters*, 28:3539 (1987); Nielsen, et al., *Tetrahedron Letters*, 29:2911 (1988); Jager et al., *Biochemistry*, 27:7237 (1988); Uznanski et al., *Tetrahedron Letters*, 28:3401 (1987); Bannwarth, *Helv. Chim. Acta.*, 71:1517 (1988); Crosstick and Vyle, *Tetrahedron Letters*, 30:4693 (1989); Agrawal, et al., *Proc. Natl. Acad. Sci. USA*, 87:1401–1405 (1990), the teachings of which are incorporated herein by reference. Other methods for synthesis or production also are possible. In a preferred embodiment the oligonucleotide is a deoxyribonucleic acid (DNA), although ribonucleic acid (RNA) sequences may also be synthesized and applied.

The oligonucleotides useful in the invention preferably are designed to resist degradation by endogenous nucleolytic enzymes. In vivo degradation of oligonucleotides produces oligonucleotide breakdown products of reduced length. Such breakdown products are more likely to engage in non-specific hybridization and are less likely to be effective, relative to their full-length counterparts. Thus, it is desirable to use oligonucleotides that are resistant to degradation in the body and which are able to reach the targeted cells. The present oligonucleotides can be rendered more resistant to degradation in vivo by substituting one or more internal artificial internucleotide linkages for the native phosphodiester linkages, for example, by replacing phosphate with sulfur in the linkage. Examples of linkages that may be used include phosphorothioates, methylphosphonates, sulfone, sulfate, ketyl, phosphorodithioates, various phosphoramidates, phosphate esters, bridged phyosphorothioates and bridged phosphoramidates. Such examples are illustrative, rather than limiting, since other internucleotide linkages are known in the art. See, e.g., Cohen, *Trends in Biotechnology* (1990). The synthesis of oligonucleotides having one or more of these linkages substituted for the phosphodiester internucleotide linkages is well known in the art, including synthetic pathways for producing oligonucleotides having mixed internucleotide linkages.

Oligonucleotides can be made resistant to extension by endogenous enzymes by "capping" or incorporating similar groups on the 5' or 3' terminal nucleotides. A reagent for capping is commercially available as Amino-Link II™ from Applied BioSystems, Inc., Foster City, Calif. Methods for capping are described, for example, by Shaw et al., *Nucleic Acids Res.*, 19:747–750 (1991) and Agrawal, et al., *Proc. Natl. Acad. Sci. USA*, 88(17):7595–7599 (1991), the teachings of which are hereby incorporated herein by reference.

Methods of Application of the Oligonucleotides

In accordance with the invention, the inherent binding specificity of antisense oligonucleotides characteristic of base pairing is enhanced by limiting the availability of the antisense compound to its intended locus in vivo, permitting lower dosages to be used and minimizing systemic effects. Thus, oligonucleotides are applied locally to achieve the desired effect. The concentration of the oligonucleotides at the desired locus is much higher than if the oligonucleotides were administered systemically, and the therapeutic effect can be achieved using a significantly lower total amount. The local high concentration of oligonucleotides enhances penetration of the targeted cells and effectively blocks translation of the target nucleic acid sequences.

The oligonucleotides can be delivered to the locus by any means appropriate for localized administration of a drug. For example, a solution of the oligonucleotides can be injected directly to the site or can be delivered by infusion using an infusion pump. The oligonucleotides also can be incorporated into an implantable device which when placed at the desired site, permits the oligonucleotides to be released into the surrounding locus.

The oligonucleotides are most preferably administered via a hydrogel material. The hydrogel is noninflammatory and biodegradeable. Many such materials now are known, including those made from natural and synthetic polymers. In a preferred embodiment, the method exploits a hydrogel which is liquid below body temperature but gels to form a shape-retaining semisolid hydrogel at or near body temperature. Preferred hydrogel are polymers of ethylene oxide-propylene oxide repeating units. The properties of the polymer are dependent on the molecular weight of the polymer and the relative percentage of polyethylene oxide and polypropylene oxide in the polymer. Preferred hydrogels contain from about 10 to about 80% by weight ethylene oxide and from about 20 to about 90% by weight propylene oxide. A particularly preferred hydrogel contains about 70% polyethylene oxide and 30% polypropylene oxide. Hydrogels which can be used are available, for example, from BASF Corp., Parsippany, N.J., under the tradename Pluronic®.

In this embodiment, the hydrogel is cooled to a liquid state and the oligonucleotides are admixed into the liquid to a concentration of about 1 mg oligonucleotide per gram of hydrogel. The resulting mixture then is applied onto the surface to be treated, e.g., by spraying or painting during surgery or using a catheter or endoscopic procedures. As the polymer warms, it solidifies to form a gel, and the oligonucleotides diffuse out of the gel into the surrounding cells over a period of time defined by the exact composition of the gel.

The oligonucleotides can be administered by means of other implants that are commercially available or described in the scientific literature, including liposomes, microcapsules and implantable devices. For example, implants made of biodegradable materials such as polyanhydrides, polyorthoesters, polylactic acid and polyglycolic acid and copolymers thereof, collagen, and protein polymers, or non-biodegradable materials such as ethylenevinyl acetate (EVAc), polyvinyl acetate, ethylene vinyl alcohol, and derivatives thereof can be used to locally deliver the oligonucleotides. The oligonucleotides can be incorporated into the material as it is polymerized or solidified, using melt or solvent evaporation techniques, or mechanically mixed with the material. In one embodiment, the oligonucleotides are mixed into or applied onto coatings for implantable devices such as dextran coated silica beads, stents, or catheters.

As described in the following examples, the dose of oligonucleotides is dependent on the size of the oligonucleotides and the purpose for which is it administered. In general, the range is calculated based on the surface area of tissue to be treated. The effective dose of oligonucleotide is somewhat dependent on the length and chemical composition of the oligonucleotide but is generally in the range of about 30 to 3000 μg per square centimeter of tissue surface area. Based on calculations using the application of antisense myb in a hydrogel to blood vessel that has been injured by balloon angioplasty in a rat model, a dose of about 320 μg oligonucleotide applied to one square centimeter of tissue was effective in suppressing expression of the c-myb gene product.

Therapeutic Applications

The method of the present invention can be used to treat a variety of disorders which are linked to or based on expression of a protein by a gene. The method is particularly useful for treating vascular disorders, particularly vascular restenosis. The following non-limiting examples demonstrate use of antisense oligonucleotides to prevent or very significantly inhibit restenosis following vascular injury such as is induced by balloon angioplasty procedures. This has been accomplished by using antisense, delivered locally, to inhibit expression of genes encoding proteins determined to be involved in vascular restenosis, including c-myb, non-muscle myosin heavy chain (NMMHC) and proliferative cellular nuclear antigen (PCNA). However, the methods of the invention have many other uses.

Expression of specific genes in specific tissues may be suppressed by oligonucleotides having a nucleotide sequence complementary to the mRNA transcript of the target gene. Both c-myb and non-muscle myosin proteins appear to be critically involved in the initiation of proliferation of smooth muscle cells. The inhibition of the production of these proteins by antisense oligonucleotides offers a means for treating post-angioplasty restenosis and chronic processes such as atherosclerosis, hypertension, primary pulmonary hypertension, and proliferative glomerulonephritis, which involve proliferation of smooth muscle cells.

Illustrative of other conditions which may be treated with the present method are pulmonary disorders such as acute respiratory distress syndrome, idiopathic pulmonary fibrosis, emphysema, and primary pulmonary hypertension. These conditions may be treated, for example, by locally delivering appropriate antisense incorporated in an aerosol by inhaler. These disorders are induced by a complex overlapping series of pathologic events which take place in the alveolus (air side), the underlying basement membrane and smooth muscle cells, and the adjacent endothelial cell surface (blood side). It is thought that the alveolar macrophage recognizes specific antigens via the T cell receptor, become activated and elaborates a variety of substances such as PDGF which recruit white blood cells as well as stimulate fibroblasts. White cells release proteases which gradually overwhelm the existing antiproteases and damage alveolar phneumocytes; fibroblasts secrete extracellular matrix which induce fibrosis. Selected growth factors such as PDGF and the subsequent decrease in blood oxygen, which is secondary to damage to the alveolar membrane, induce smooth muscle growth. This constricts the microvascular blood vessels and further decreases blood flow to the lung. This further decreases the transport of oxygen into the blood. The molecular events outlined above also induce activation of the microvascular endothelial cell surface with the appearance of selectins and integrins as well as the appearance of tissue factor which initiates blood coagulation. These selectin and integrin surface receptors allow white blood cells to adhere to microvascular endothelial cells and release proteases as well as other molecules which damage these cells and allow fluid to accumulate within the alveolus. The above events also trigger microvascular thrombosis with closure of blood vessels. The end result of this process is to further impede oxygen exchange.

Antisense oligonucleotides, locally delivered to the alveolar/microvascular area, could be directed against the following targets to intervene in the pathology outlined above, since the cDNA sequences of all of the targets selected are known. Thus, antisense oligonucleotides specific for mRNA transcribed from the genes would inhibit production of the alveolar macrophage T cell receptor to prevent initiation of the above events; inhibit product of a protein to prevent activation of alveolar white cells, or inhibit production of elastase to prevent destruction of alveolar membrane; inhibit production of PDGF to prevent recruitment of white cells or resultant fibrosis; inhibit production of c-myb to suppress SMC proliferation; inhibit production of p-selectin or e-selectin or various integrins to prevent adhesion of blood white cells to pulmonary microvascular endothelial cells; or inhibit the production of tissue factor and PAI-1 to suppress microvascular thrombosis.

As additional examples, Tissue Factor (TF) is required for coagulation system activation. Local application of antisense targeting the mRNA or DNA of a segment of TF in the area of clot formation can prevent additional coagulation. This therapy can be employed as an adjunct to or as a substitute for systemic anticoagulant therapy or after fibrinolytic therapy, thereby avoiding systemic side effects.

Plasminogen activator inhibitor (PAI-1) is known to reduce the local level of tissue plasminogen activator (TPA). The human cDNA sequence for PAI-1 is known. Local application of antisense targeting the mRNA or DNA of PAI-1 should permit a buildup of TPA in the targeted area. This may result in sufficient TPA production to naturally lyse the clot without systemic side effects.

A combination of antisense-TF and antisense-PAI-1 may be utilized to maximize the efficacy of treatment of several disorders, including local post thrombolytic therapy and preventative post-angioplasty treatment.

Many other vascular diseases can be treated in a manner similar to that described above by identifying the target DNA or mRNA sequence. The treatment of diseases which could benefit using antisense therapy include, for example, myocardial infarction, peripheral muscular disease and peripheral angioplasty, thrombophlebitis, cerebro-vascular disease (e.g., stroke, embolism), vasculitis (e.g., temporal ateritis) angina and Budd-Chiari Syndrome.

The following Examples are included by way of illustration, and are not intended to limit the scope of the invention.

EXAMPLES

Materials and Methods

SV40LT-SMC (rat smooth muscle cells, gift of Dr. C. Reilly, Merck, Sharp and Dohme, West Point, Pa.) were grown in Dulbecco's modified Eagle's Medium (DMEM) supplemented with 10% heat-inactivated fetal bovine serum (Gibco-BRL, Bethesda, Md.). BC3H1 mouse smooth muscle cells (ATCC CRL 1443, obtained from the American Type Culture Collection, Rockville, Md.) were grown in DMEM supplemented with 20% heat-inactivated fetal bovine serum (FBS). The cells were cultured at 37° C. in a humidified 5% $CO_2$ atmosphere.

Primary aortic smooth muscle cells (SMC) were isolated by the explant technique from Sprague-Dawley rats (average weight 350 g) and FVB mice (average weight 50 g). Ross, *J. Cell Biol.*, 50:172–186 (1971). The cultures exhibited typical morphological characteristics of vascular SMC (spindle shape and hill-and-valley pattern). Identification of vascular SMC was confirmed by Northern analysis demonstrating the presence of the smooth muscle alpha actin isoform. Primary aortic SMC were used in the second passage.

Antisense and sense 18-mer phosphorothioate oligonucleotides were synthesized on an ABI DNA synthesizer. Oligonucleotides were deprotected on the machine, dried down, resuspended in "TE" (10 mM Tris, pH 7.5, 1 mM EDTA, pH8.0) and quantified by spectrophotometry and gel electrophoresis. The following sequences were employed:

Antisense c-myb oligonucleotide:

Sequence ID NO. 1

GTGTCGGGGTCTCCGGGC

Antisense NMMHC oligonucleotide:

Sequence ID No. 2

CATGTCCTCCACCTTGGA

Antisense thrombomodulin ("TM") oligonucleotide:

Sequence ID No. 3

ACCCAGAAAGAAAATCCCAAG and, Antisense human c-myb oligonucleotide, which has 2 mismatches compared with mouse c-myb:

Sequence ID No. 4

GTGCCGGGGTCTTCGGGC.

The Sequence ID No. 1 is complementary to nucleotides 4–22 of mouse c-myb (Bender et al., (1986) *Natl. Acad. Sci. USA*,83:3204–3208); Sequence ID No. 2 is complementary to nucleotides 232–250 of human NMMHC-A (Simons et al., (1991) *Cir. Res.*,69:530–539); and Sequence ID No. 3 is complementary to nucleotides 4–25 of mouse TM (Dittman and Majerus, (1989) *Nucl. Acid Res.*,17:802). Sequence ID No. 4 is complementary to a human c-myb sequence and has 2 base mismatches compared with murine c-myb. The NMMHC sequence was chosen in a region with the closest degree of homology between known nonmuscle myosin sequences. The sequence has 1 nucleotide difference with a human NMMHC-B (Simons et al., ibid.) and 2 nucleotide differences with chicken NMMHC-A and NMMHC-B. The corresponding sense sequences were used as controls.

Example 1: Inhibition of c-myb and NMMHC-A using antisense oligonucleotides in vitro.

Growth Assay

Both cell lines as well as early passage primary aortic SMC were seeded at a density of 25,000 cells per well in cluster 6 well plates (Costar, Cambridge, Mass.) in 10% FBS-DMEM (20% FBS-DMEM for BC3H1 cells). The following day, the cells were washed twice with phosphate-buffered saline (PBS), the media was replaced with 0.5% FBS-DMEM growth arrest media, and the cells were kept in growth-arrest media for 96 hours. The media then was changed to 10% or 20% FBS-DMEM, and synthetic c-myb and NMMHC antisense and sense oligonucleotides were added. The cells were permitted to grow for 72 hours, trypsinized and counted on a Coulter Counter.

Alternatively, the two cell lines and the SMC cells were allowed to proliferate in 10% or 20% FBS-DMEM, oligonucleotides were added, and cell counts were obtained after 5–8 days as described above. Each experiment was carried out in triplicate and repeated at least two additional times. Data is expressed as mean±standard deviation.

The results (shown in FIG. 1) showed that, in vitro, antisense oligonucleotides to both c-myb (Seq. ID No. 1) and NMMHC (Seq. ID No. 2) caused substantial suppression of cellular proliferation while the sense oligonucleotides had no effect and were similar to the results obtained using just Tris-EDTA buffer.

The oligonucleotides utilized were derived from the nucleotide sequences of human/chicken NMMHC or mouse c-myb cDNAs. The importance of the specificity of the antisense oligonucleotides was shown by the complete loss of antiproliferative action when two bases of the 18 base c-myb antisense sequence were randomly altered (Seq. ID No. 4). The results for this test were as follows: antisense c-myb: 475,600 cells±25,000 cells; mismatch antisense c-myb: 958,800 cells±12,000 cells; sense c-myb: 935,200 cells±22,000 cells. Thus, the mismatch antisense c-myb (seq. ID No. 4) failed to inhibit proliferation of SMC cells significantly. The antisense and sense phosphorothiolate thrombomodulin (TM) oligonucleotides had no apparent effect on SMC growth (antisense TM: 364,580 cells±19,000 cells vs sense TM: 376,290 cells±11,000 cells).

The inhibitory action of antisense phosphorothiolate oligonucleotides directed against NMMHC as compared to c-myb was more clearly concentration-dependent (antisense NMMHC: 32% vs 65% suppression at 2 µM and 25 µM, respectively; antisense c-myb: 33% vs 50% suppression at 2 µM and 25 µM respectively). Previous estimates of the relative abundance of these two messages indicated that c-myb mRNA occurs at extremely low concentrations in exponentially growing SMC (less than 0.01% of poly A+ RNA), whereas NMMHC mRNA is present at significantly higher levels. The observed concentration dependence of the two antisense oligonucleotides with regard to growth inhibition was consistent with the relative abundance of the two mRNAs.

Figure 2B:
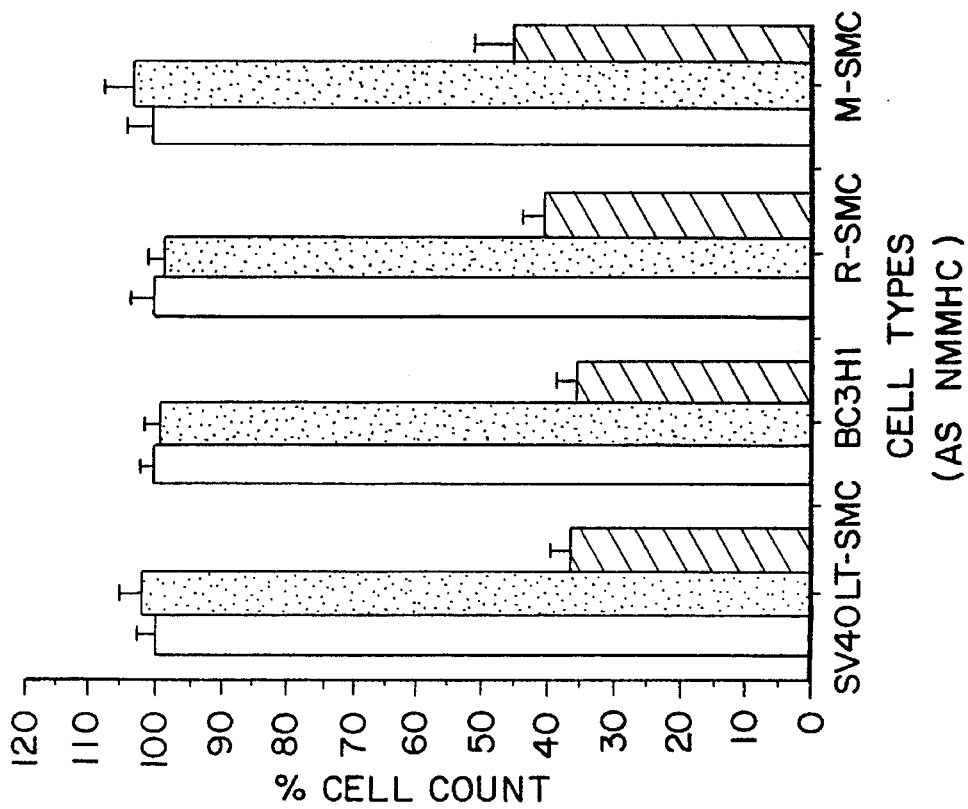
FIGS. 2A and 2B are graphs of the cell count for SV40TL-SMC cells, BC3H1 cells, rat aortic SMC, and mouse aortic SMC treated with antisense HNMMHC (A) and c-myb (B).
Figure 2A:
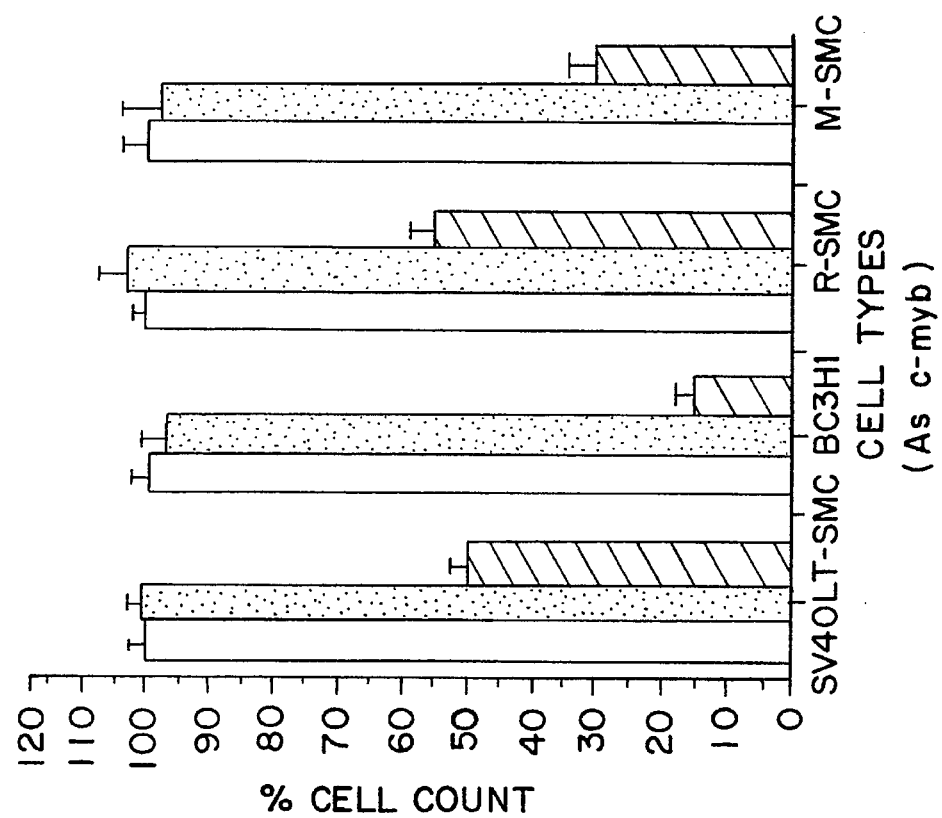

The antiproliferative effects of the antisense and sense phosphorothiolate oligonucleotides were also evaluated with the BC3H1 cell line as well as with primary rat and mouse aortic SMC. The data obtained showed that growth of the three cell types is greatly suppressed with phosphorothiolate antisense but not sense NMMHC or c-myb oligonucleotides (FIG. 2). Antisense c-myb oligonucleotides exhibited a greater antiproliferative effect on mouse aortic SMCs and mouse BC3H1 cells as compared to rat aortic SMC and rat SV40LT-SMC (FIG. 2B). The difference in growth inhibition is most likely attributable to the greater extent of antisense nucleotide mismatch between rat and mouse c-myb sequences within the chosen area.

The minimal time required for exposure of SV40LT-SMC to antisense NMMHC or c-myb phosphorothiolate oligonucleotides to achieve maximal growth inhibition was determined. In the studies cited above, cells were continuously exposed to oligonucleotides from the time of shift from growth arrest media by addition to 10%FBS-DMEM to the measurement of antiproliferative effect by cell count at 72 hr. In the experiments cited below, SV40LT-SMC were treated with antisense oligonucleotides for stated periods after the shift from growth arrest, washed twice with PBS, placed in fresh oligonucleotide free 10% FBS-DMEM, and assessed for growth inhibitory effect by cell count at 72 hr. The results, shown in FIG. 3A showed that the addition of 25 µM antisense NMMHC or c-myb oligonucleotides for as little as 1 hr, generated a significant antiproliferative effect. After 2 hr of treatment with antisense NMMHC oligonucleotides, the extent of growth inhibition is equivalent to that obtained by continuous exposure for 72 hr (65% suppression of cell growth). The admixture of antisense c-myb oligonucleotides for 4 hr produced an antiproliferative effect which is identical to that observed with continuous exposure for 72 hr (50% suppression of cell growth).

An experiment was performed to determined whether the growth inhibitory effects of antisense phosphorothiolate oligonucleotides are readily reversible. To this end, SV40LT-SMC were exposed for 4 hr after release from growth arrest to 25 µM antisense or sense NMMHC or c-myb oligonucleotides. The cells were subsequently washed twice with PBS, placed in fresh oligonucleotide free 10% FBS-DMEM media, and cell counts were determined at day 3 and day 5. The data revealed that proliferation of SV4OLT-SMC treated with antisense NMMHC or c-myb, as compared to the corresponding sense oligonucleotides, demonstrated a significant initial suppression of growth at day 3 of about 65% and 50%, respectively. However, the doubling times, between day 3 and day 5 of the SV40LT-SMC treated with antisense NMMHC or c-myb, as compared to the corresponding sense oligonucleotides, were identical at 22 hrs.

Figure 3B:
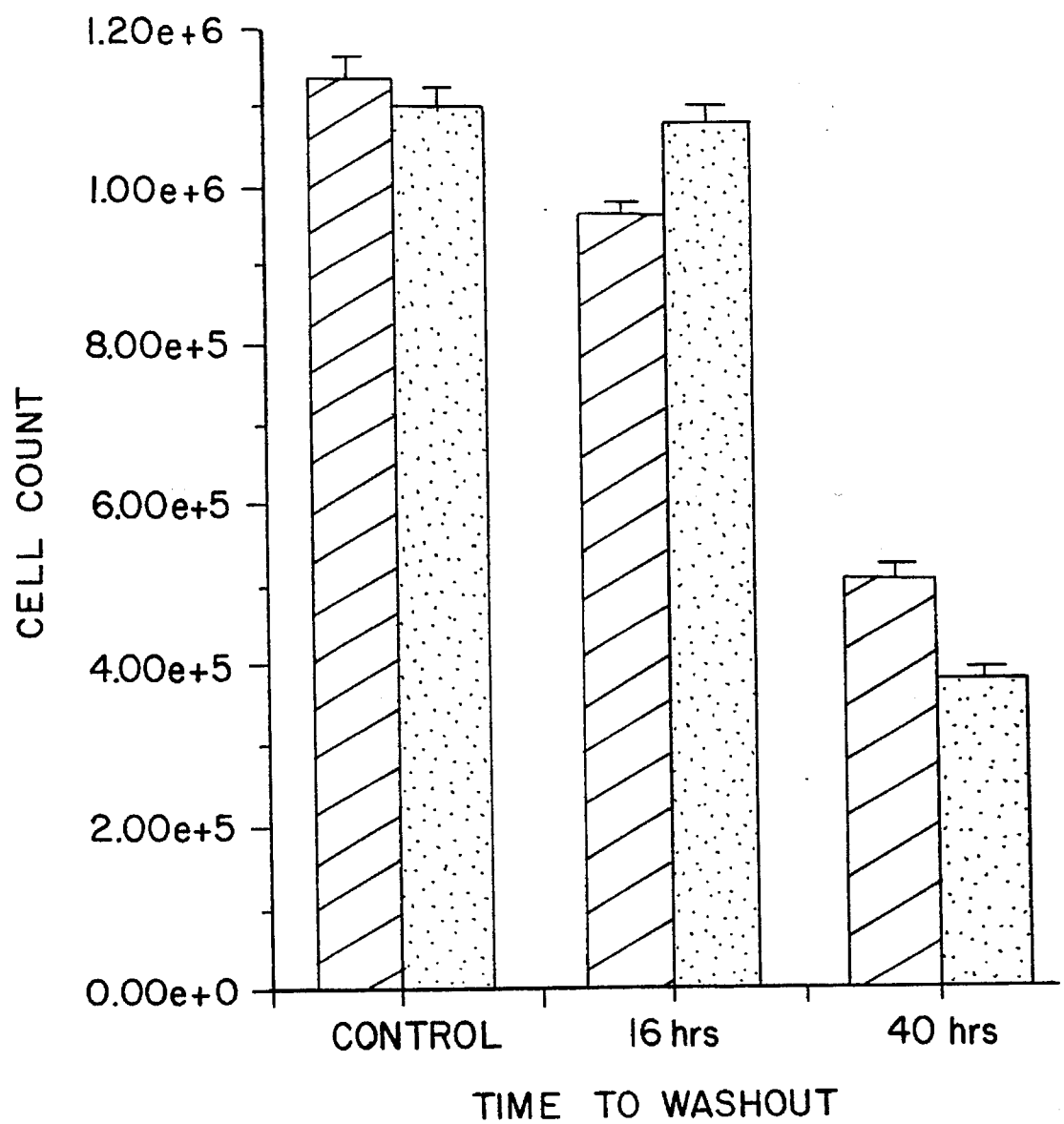
FIG. 3B is a bar graph showing the effect on SV-SMC cells treated with unmodified antisense c-myb (light bar) and NMMHC (dark bar) for 16 hours and 40 hours after release from growth arrest.

Treatment of SV40LT-SMC with 25 µM unmodified antisense NMMHC or c-myb oligonucleotides for 16 hr after release from growth arrest, produced no discernible antiproliferative effect at 72 hr. In contrast, the continuous exposure for 40 hr to the two oligonucleotides, at identical levels, resulted in the same growth inhibitory effect observed with the phosphorothiolate derivatives (FIG. 3B).

The importance of growth arrest to the antiproliferative potency of antisense NMMHC and c-myb phosphorothiolate oligonucleotides also was evaluated. SV40LT-SMC were allowed to grow exponentially while continuously exposed to 10 µM antisense NMMHC or c-myb oligonucleotides and cell counts were determined at 72 hr and 120 hr. The treatment of SMC with antisense NMMHC oligonucleotides produced no growth inhibitory effect at either time point, whereas exposure to antisense c-myb oligonucleotides generated a 19% suppression of proliferation at 72 hr and a 40% suppression of proliferation at 120 hr.

RNA Analysis

Total cellular RNA was determined from SV40LT-SMC cells in culture 24 hours after growth induction with 10% FBS in DMEM using the method of Chomzynski and Sacchi, *J. Cell. Physiol.*, 142:342 (1990). The RNA was quantified by spectrophotometry and a total of 10 µg was applied to nitrocellulose using a dot blot apparatus. The blot was then hybridized with a random primed c-myb, NMMHC, large T-antigen, GAPDH and TM probes in 10% dextran sulfate and 40% formamide for 16 hours at 42° C. Northern blots and RNA dot blots were washed in SSC solution with final washes performed at 50° C. and 0.5×SSC for c-myb, 55° C. and 0.2×SSC for NMMHC, 55° C. and 0.2×SSC for large T antigen, 50° C. and 0.2×SSC for GADPH and 50° C. and 0.2×SSC for TM. The Northern blots were subjected to autoradiography. The RNA blots were quantified by normalizing c-myb or GAPDH message counts to large T-antigen counts using a Betascope 603 analyzer (Betagen, Waltham, Mass.). The numbers represent total counts for each dot. The entire experiment was repeated twice. Results are for cells treated with sense c-myb oligonucleotide (25 µM); antisense c-myb oligonucleotide (25 µM); and heparin (100 µg/ml). The cells were allowed to reach confluence and become quiescent for two days.

Figure 4:
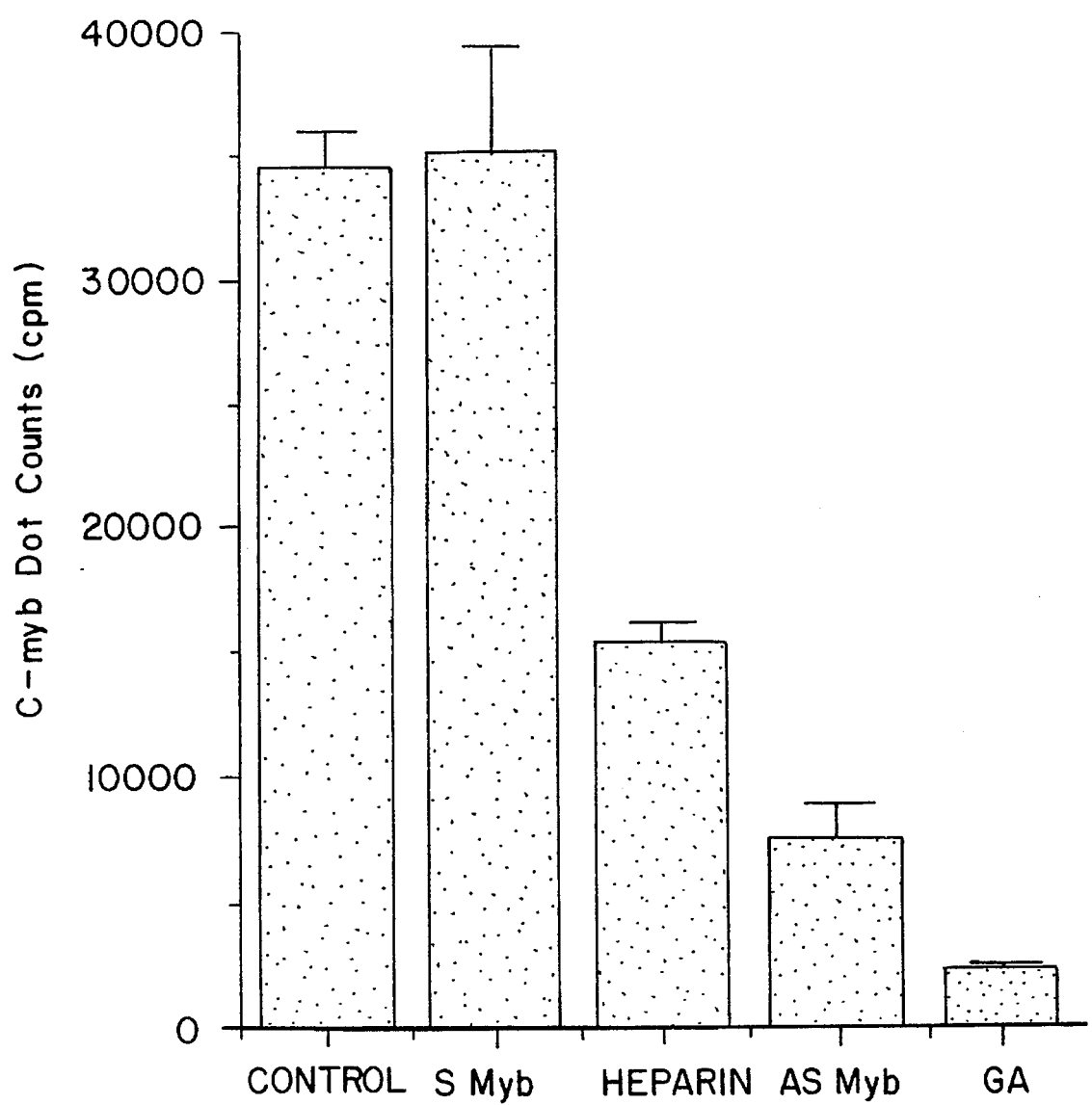
FIG. 4 is a bar graph of the results of a c-myb RNA dot blot, showing the amount of mRNA present in SV-SMC cells treated with sense c-myb (S Myb), antisense c-myb (AS Myb) and heparin compared with untreated (control) and growth-arrested (GA) cells.

Cells exposed to antisense c-myb oligonucleotide had a markedly decreased amount of c-myb message present as assessed by RNA dot blot hybridization with a radiolabeled c-myb probe. The results are shown in FIG. 4. FIG. 4 shows individual dot counts, adjusted for the quantity of RNA in each sample, for synchronized proliferating SV-SMCs treated with sense c-myb (S Myb) and antisense c-myb (AS Myb), heparin-arrested (heparin), and growth-arrested (GA) cells. Cell growth was arrested with antisense c-myb to about the same degree as with heparin had similar amounts of c-myb message present. Similarly, antisense NMMHC oligonucleotide led to a marked attenuation of the NMMHC message detected on a Northern blot.

The amount of c-myb protein in the cells treated with antisense c-myb was markedly reduced, as was the non-muscle myosin protein in cells treated with antisense NMMHC-B, as assessed by indirect immunofluorescence.

Immunofluorescence Microscopic Examination of SMC for c-myb and nonmuscle myosin SV40LT-SMC were fixed with 2% formaldehyde/PBS at room temperature for 15 minutes, permeated with 2% Triton X-100/PBS, washed 3 times with 1% BSA/PBS and exposed for 2–4 hr to anti-myb or anti-NMMHC antisera diluted 1:250 or 1:1000 in 1% BSA/PBS. The anti-myb antisera was obtained from Cambridge Research Laboratories (Wilmington, Del.) and was generated by immunizing rabbits with the synthetic peptide His-Thr-Cys-Ser-Tyr-Pro-Gly-Trp-His-Ser-Thr-Ser-Ile-Val corresponding to mouse c-myb amino acid residues 332–345. The anti-nonmuscle myosin antiserum was kindly provided by RS Adelstein and JS Sellers (LMC, NIH, Bethesda, Md.) and was generated by immunizing rabbits with purified human platelet myosin. This antiserum is monospecific as judged by Western blot analysis. The cells were washed three times with 1% BSA/PBS to remove excess primary antibody followed by incubation for 2 hr with second antibodies diluted 1:100 in 1% BSA/PBS (rhodamine-conjugated goat anti-rabbit IgG and FITC-conjugated sheet anti-rabbit purchased from Organon Teknika, Durham, N.C.). After washing cells three times with 1% BSA/PBS, the samples were examined with a Nikon Optiphot fluorescence photomicroscope.

The reduction in the concentrations of NMMHC and c-myb mRNAs induced by antisense oligonucleotides should lead to a decrease in the levels of the specific proteins. To show this effect, SV40LT-SMC cells were plated at low density (10,000/cm$^2$) on a 2 well glass slides (Nunc, Inc., Naperville, Ill.), growth-arrested for 96 hr in 0.5% FBS-DMEM and then shifted to 10% FBS-DMEM to which were added 25 µM antisense or sense NMMHC or c-myb phosphorothiolate oligonucleotides. After 24 hr (c-myb) or 72 hr (NMMHC), SMC were examined by indirect immunofluorescence microscopy utilizing specific antisera against NMMHC or c-myb. It was readily apparent that the concentrations of NMMHC or c-myb proteins in most cells treated with antisense oligonucleotides were dramatically reduced as compared to those exposed to sense oligonucleotides. However, it was also clear that occasional cells in each panel displayed substantial amounts of protein. This observation was probably secondary to the premature escape of this subpopulation from growth arrest and the subsequent augmentation in their levels of target mRNAs. The specificity of the immunofluorescence technique was documented by carrying out the above procedure with untreated SMC in the absence of primary antibody or in the presence of a large excess of purified antigen which showed minimal background signal.

Example 2: Release of oligonucleotides from polymeric matrices.

Release of Oligonucleotides from Pluronic™ Gel Matrix

Matrices made from a poly (ethylenoxide-propyleneoxide) polymer containing c-myb and NMMHC antisense oligonucleotides (described in Materials and Methods) were prepared in order to test the rate of release of the oligonucleotides from the matrices. The test samples were prepared by weighing 1.25 g of UV sterilized Pluronic™ 127 powder (BASF Corp., Parsippany, N.J.) in scintillation vials and adding 3.25 ml of sterile water. Solubilization was achieved by cooling on ice while shaking. To these solutions were added 500 µl of a sterile water solution containing the oligonucleotides (5.041 mg/500 µl). The final gels contained 25% (w/w) of the polymer and 1 mg/g oligonucleotides.

Figure 5:
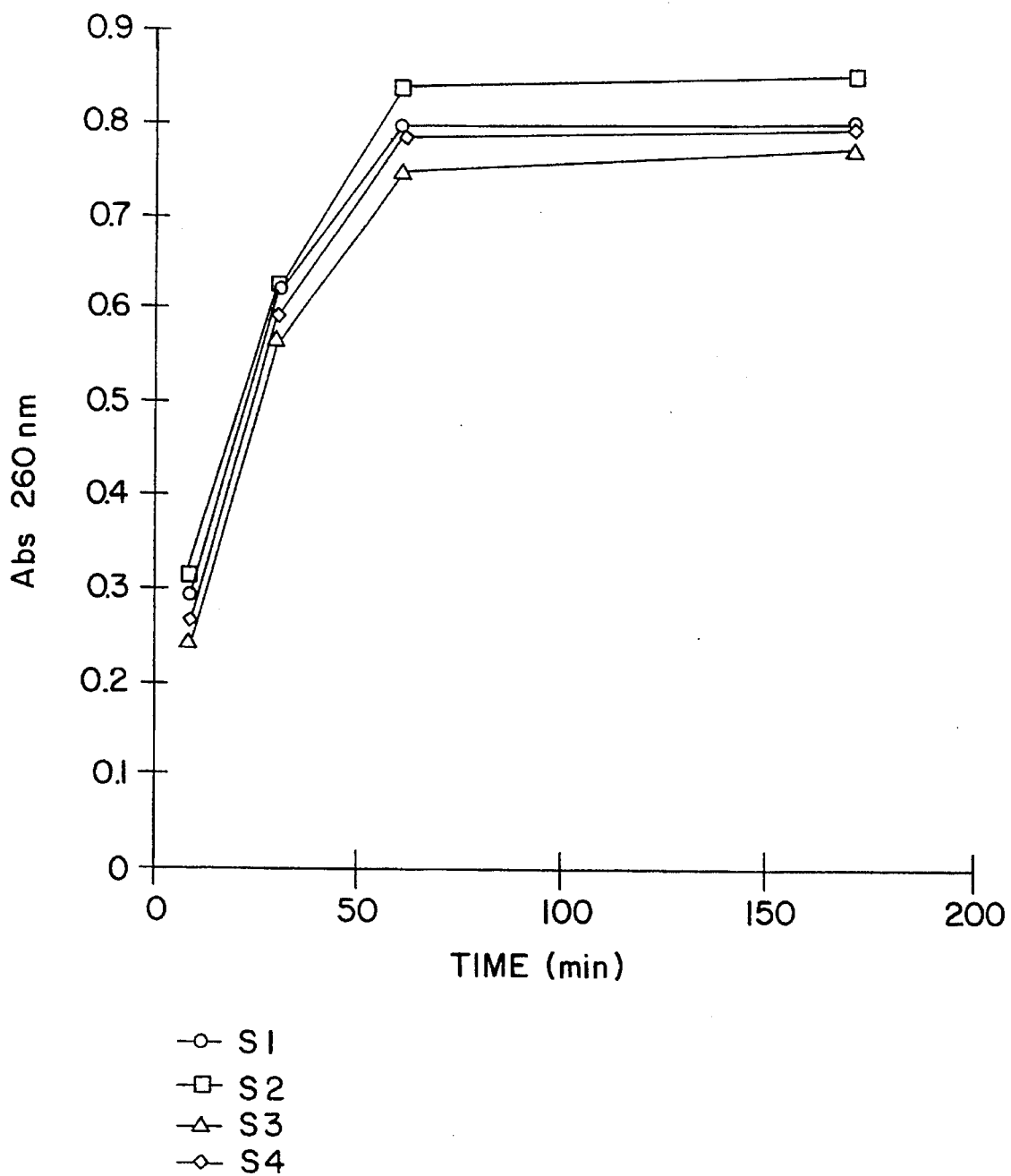
FIG. 5 is a graph showing the release kinetics of oligonucleotides from a Pluronic™ 127 gel matrix.

The release kinetics of the gels containing oligonucleotides were determined by placing the gels in PBS and measuring the absorption ($OD_{260}$) over time. The results for four test gels, shown in FIG. 5, indicate that oligonucleotides are released from the gels in less than one hour.

Release of oligonucleotides from EVAc matrices

The release of oligonucleotides from ethylene vinyl acetate (EVAc) matrices was demonstrated.

Matrices were constructed and release was determined as described by Murray et al. (1983), *In Vitro.*, 19:743–748. Ethylene-vinyl acetate (EVAc) copolymer (ELVAX 40P, DuPont Chemicals, Wilmington, Del.) was dissolved in dichloromethane to form a 10% weight by volume solution. Bovine serum albumin and the oligonucleotide were dissolved together at a ratio of 1000–2000:1 in deionized $H_2O$, frozen with liquid $N_2$ and then lyophilized to form a dry powder. The powder was pulverized to form a homogeneous distribution of particles less than 400 microns in diameter. A known quantity of the powder was combined with 4–10 ml of the 10% (w/v) EVAc copolymer solution in a 22 ml glass scintillation vial. The vial was vortexed for 10 seconds to form a homogeneous suspension of the drug particles in the polymer solution. This suspension was poured onto a glass mold which had been precooled on a slab of dry ice. After the mixture froze it was left in place for 10 minutes and then removed from the mold and placed into a –20° C. freezer for 2 days on a wire screen. The slab was dried for an additional 2 days at 23° C. under a 600 millitorr vacuum to remove residual dichloromethane. After the drying was complete 5 mm×0.8 mm circular slabs are excised with a #3 cork borer.

Figure 6:
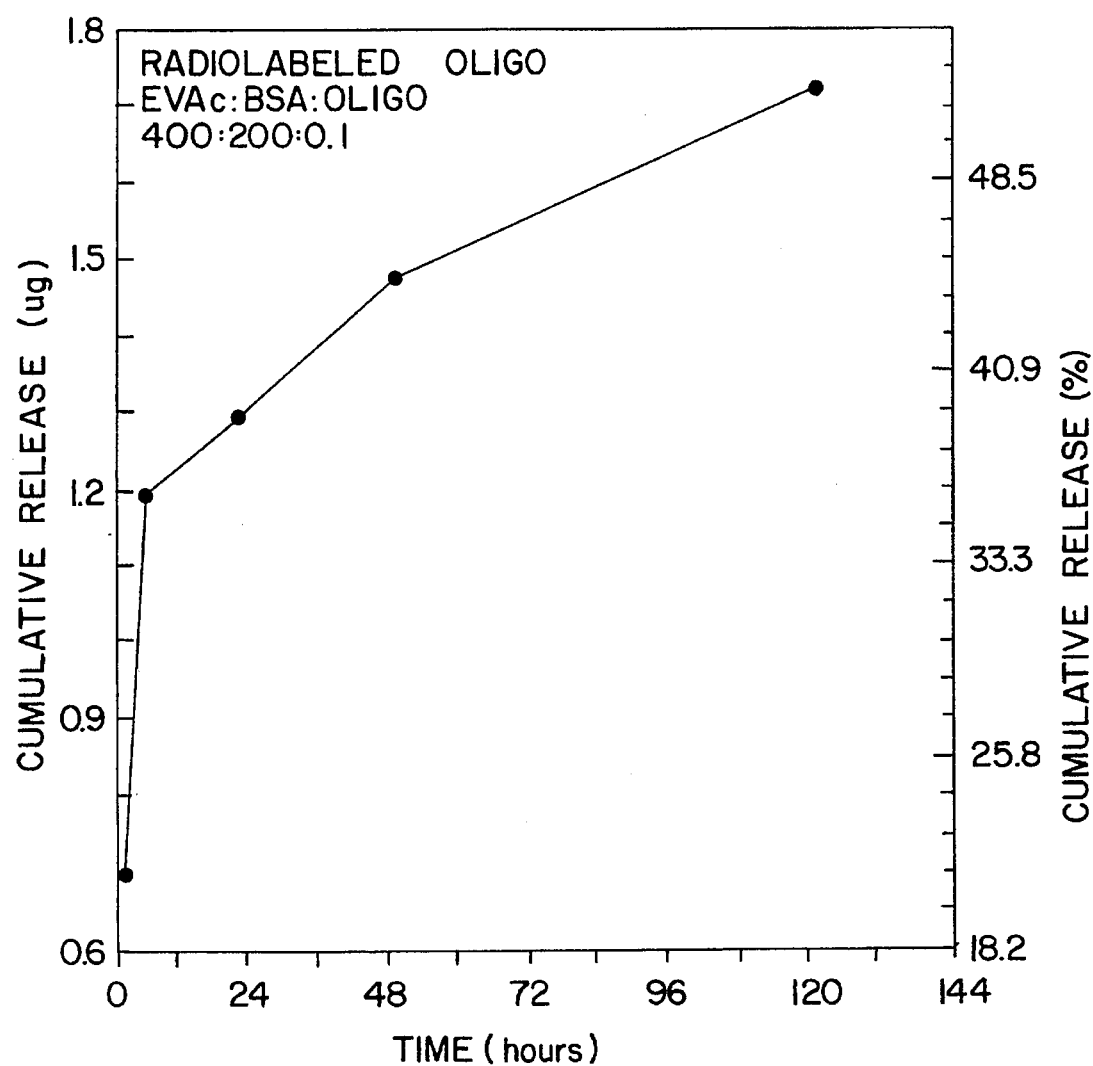
FIG. 6 is a graph showing the release kinetics of oligonucleotides from an EVAc matrix.

The results, shown in FIG. 6, indicate that about 34% of the oligonucleotide was released within the first 48 hours.

Example 3: In vivo application of oligonucleotides to inhibit c-myb and NMMHC in rats.

I. Animal Model.

Balloon stripping of the rat carotid artery is used as a model of restenosis in vivo. Rats were anesthetized with Nembutal (50 mg/kg). A left carotid dissection was carried out and a 2F Fogarty catheter was introduced through the arteriotomy incision in the internal carotid artery. The catheter was advanced to the aortic arch, the balloon was inflated and the catheter withdrawn back to the arteriotomy site. This was repeated two more times. Subsequently, the balloon being withdrawn, the internal carotid was tied off, hemostasis achieved, and the wound closed.

II. Oligonucleotide Delivery.

The oligonucleotides were applied with a hydrogel and with an implantable ethylene vinyl acetate (EVAc) matrix. A polyethylene oxide-polypropylene oxide polymer (Pluronic™ 127, BASF, Parsippany, N.J.) was used as a hydrogel. The Pluronic™ gel matrices were prepared as described in Example 2. Briefly, sterile solutions of Pluronic™ 127 were prepared by weighing 1.25 g of UV sterilized Pluronic powder into a scintillation vial and adding 3.25 ml of sterile water. Solubilization was achieved by cooling on ice while shaking, forming a solution containing 27.7% by weight of the polymer. To these solutions were added 500 µL of a sterile water solution of the antisense c-myb (See Example 1) oligonucleotides (5.041 mg/500 µL). The final gels were 25% w/w of Pluronic™ polymer and 1 mg/g oligonucleotide. Drug-free 25% (w/w) gels were prepared as controls. The EVAc matrices were prepared as described in Example 2, and contained 40 µg of oligonucleotide.

Immediately after balloon injury, 200 µl of Pluronic/oligonucleotide solution (which contained 200 µg of the oligonucleotide) was applied to the adventitial surface of the artery and gelling was allowed to occur. The antisense/EVAc matrix (which contained 40 μg of the oligonucleotide) and drug-free gels were applied in the same manner.

III. Quantification of Effect.

After 14 days, the animals were sacrificed and the carotid arteries were perfused under pressure (120 mmHg) with Ringer's Lactate. Both carotid arteries were excised and fixed in 3% formalin. Thin sections were then prepared for light microscopy in a standard manner. The slide was visualized and digitized using a dedicated computer system and by a hand held plenymeter and the area of neointimal proliferation calculated (in sq mm).

Figure 7:
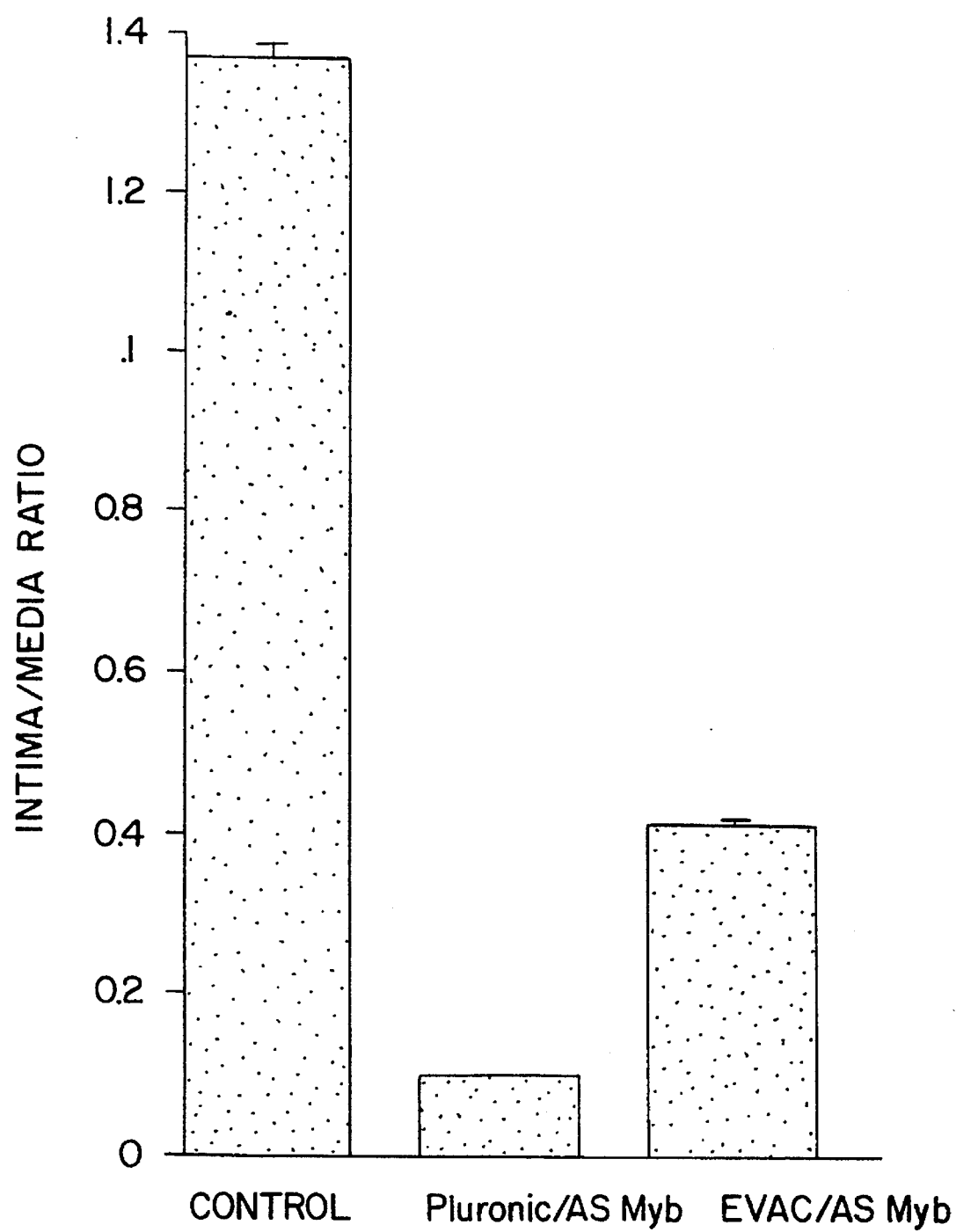
FIG. 7 is a bar graph of the effect on rat arteries of antisense c-myb (AS Myb) using a Pluronic™ gel and ethylene vinyl acetate matrix (EVAc) as the delivery systems for application of the oligonucleotides to the injured artery, versus intima/media ratio, a measure of neo-intimal proliferation.

The results are shown in FIG. 7. In control animals which received no treatment, or which were treated with the drug-free gel, there was extensive restenosis, characterized by symmetric neointimal formation along the entire length of the injured artery, narrowing the lumen by about 60%, resulting in an intima/media ratio of 1.4.

In animals treated with antisense c-myb oligonucleotides, there was minimal restenosis, minimal proliferative rim (less than 10% of the lumen) that was limited to the portion of the artery in direct contact with oligonucleotide, with an intima/media ratio of 0.09. As shown in FIG. 7, this effect was most pronounced for animals treated with the antisense/Pluronic®. The intima/media ratio obtained using EVAc/antisense was about 0.45. However, the EVAc matrix contained 40 μg of oligonucleotide, compared with 200 μg of oligonucleotide administered in the Pluronic gel, which may account for some of the difference.

Figure 8:
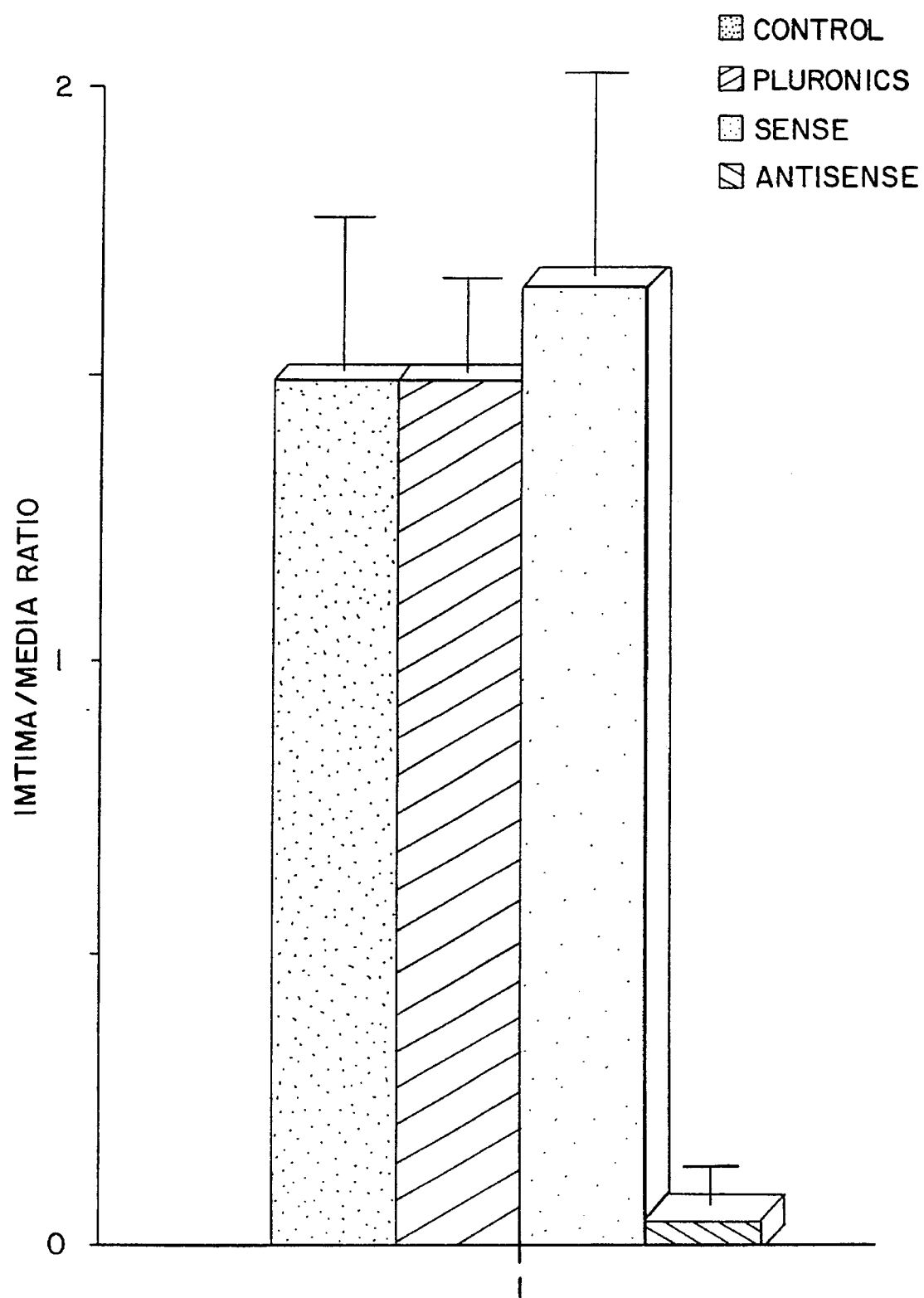
FIG. 8 is a bar graph of the effects on rat arteries of antisense c-myb applied using a Pluronic™ gel compared to a drug-free gel, a gel containing sense c-myb and an untreated artery.

FIG. 8 shows the results of extension of this experiment, in which 28 rats were treated as described above. Seven rats in each treatment group were subjected to balloon angioplasty, and the arterial walls treated as follows: with a drug free hydrogel (Pluronic™ 127 as described above), a hydrogel containing sense c-myb, a hydrogel containing antisense c-myb, and no treatment at all. As shown in FIG. 8, similar high levels of neointimal proliferation occurred in all animals except those treated with antisense c-myb, where the levels of proliferation were dramatically lower.

Example 4: Inhibition of PCNA using antisense oligonucleotides.

Using the same methodology as in Example 1, antisense for PCNA having the sequence:

Sequence ID No. 5:

GAT CAG GCG TGC CTC AAA, was applied to SV-SMC cells in culture. Sense PCNA was used as a negative control; NMMHC-B was used as a positive (inhibitory) control.

There was no suppression of smooth muscle cell proliferation in the negative control; there was 52% suppression using antisense NMMHC-B and 58% suppression with antisense PCNA.

Example 5: In vivo application of antisense oligonucleotides to inhibit smooth muscle cell proliferation in rabbits.

New Zealand white rabbits (1–1.5 Kg) were anesthetized with a mixture of ketamine and zylazine and carotid dissection was performed as described in Example 3. A 5F Swan-Ganz catheter was inserted and positioned in the descending aorta with fluoroscopic guidance. The Swan-Ganz catheter was exchanged over the wire for an angioplasty catheter with a 3.0 mm balloon. The common iliac artery was angioplastied 3 times at 100 PSI for 90 seconds each time. A Wolinsky catheter was introduced and loaded with oligonucleotide solution in a total volume of 5 cc normal saline. Saline was injected as a control in a counterlateral iliac artery. The oligonucleotides were a mixture of antisense mouse c-myb and human NMMHC (200 μM of each), described above. The mixture was injected under 5 atmospheres of pressure over 60 seconds. Two rabbits were treated with antisense oligonucleotide.

The animals were sacrificed 4 weeks later and the arteries were processed as described in Example 3 for rat arteries.

Figure 9:
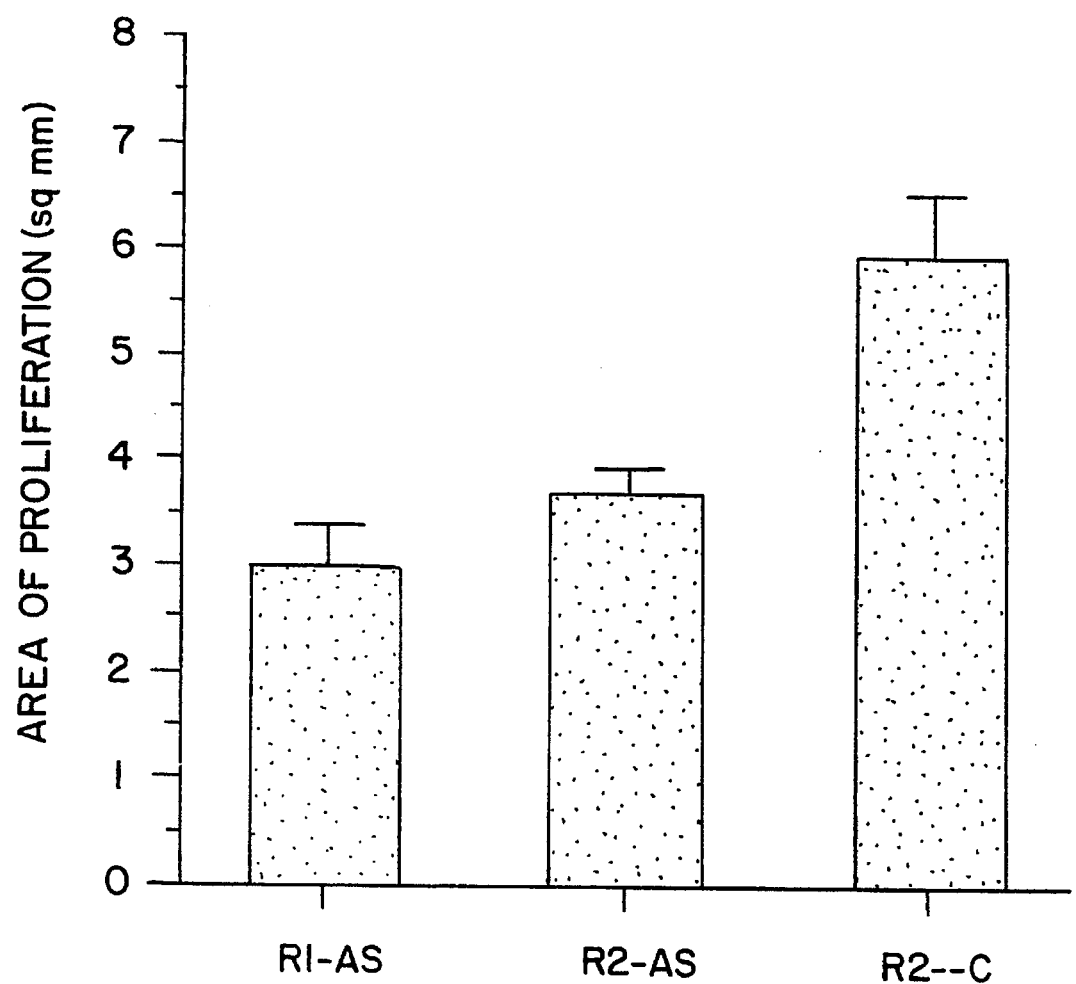
FIG. 9 is a bar graph showing the effect on rabbit arteries of a mixture of antisense c-myb and human NMMHC (200 μM each) on the proliferation of cells in the artery after balloon angioplasty.

The results, shown in FIG. 9 indicated a 50% reduction is neointimal proliferation in rabbit arteries treated with antisense compared to saline alone.

Example 6. Inhibition of proliferation of baboon smooth muscle cells using antisense oligonucleotides.

Using the same methodology as in Example 1, primary baboon smooth muscle cells (gift from Dr. Hawker, Emory University) were treated with antisense human myb (Seq. ID No. 4) and human NMMHC (Seq. ID No. 2). The cells were allowed to grow for 72 hours after treatment with the oligonucleotides, then counted as described in Example 1. The results show that hNMMHC caused 65.5% growth suppression and c-myb caused 59.77% growth suppression in the baboon cells.

Equivalents

One skilled in the art will recognize several equivalents, modifications, variations of the present method from the foregoing detailed description. Such equivalents, modifications and variations are intended be encompassed by the following claims.

We claim:

1. A method of inhibiting translation of a target nucleic acid sequence preferentially at a vascular tissue locus in vivo to thereby inhibit restenosis at said locus, the method comprising:

directly applying to said vascular tissue locus within the body of a mammal an antisense oligonucleotide, comprising 14 to 38 nucleotide bases, that is complementary to a target nucleic acid sequence expressed in smooth muscle cells and necessary to initiate a target nucleic acid sequence expressed in smooth muscle cells and necessary to initiate or support proliferation thereof, in an amount sufficient to penetrate smooth muscle cells of the tissue at said locus, to hybridize with said target nucleic acid, and to inhibit intracellular translation of said target sequence to thereby inhibit restenosis at said locus, wherein said target nucleic acid is a gene coding for a protein selected from the group consisting of c-myb, NMMHC and PCNA.

2. The method of claim 1 wherein the oligonucleotide is in a physiologically compatible solution and wherein it is applied by injection.

3. The method of claim 1 wherein the solution is applied to the tissue using an infusion pump, stent, or catheter.

4. The method of claim 1 wherein the oligonucleotide is treated to render it resistant to degradation or extension by intracellular enzymes.

5. The method of claim 4 wherein the treatment comprises substituting at least one backbone phosphodiester linkage of the oligonucleotide with a linkage selected from the group consisting of phosphorothioate, methylphosphonate, sulfone, sulfate, ketyl, phosphorodithioate, phosphoramidate, phosphate ester, bridged phosphorothioate and bridged phosphoramidate linkages.

6. The method of claim 4 wherein the treatment comprises capping a 3'-nucleotide with a structure resistant to addition of nucleotides.

7. The method of claim 1 wherein the oligonucleotide is delivered to the tissue in a concentration of between approximately 30 and 3000 µg oligonucleotide per square centimeter of tissue surface area.

8. The method of claim 1 wherein the target nucleic acid sequence comprises an mRNA.

9. A method of inhibiting translation of a target nucleic acid sequence preferentially at a vascular tissue locus in vivo to thereby inhibit restenosis at said locus, the method comprising:

directly depositing onto a surface of a vascular tissue locus within the body of a mammal an antisense oligonucleotide of 14 to 38 nucleotide bases that is complementary to a target nucleic acid sequence expressed in smooth muscle cells and necessary to initiate or support proliferation thereof, said oligonucleotide being incorporated within a carrier; and permitting the oligonucleotide to penetrate from said carrier into smooth muscle cells of the tissue at said locus in an amount sufficient to hybridize with said target nucleic acid and to inhibit intracellular translation thereof to inhibit restenosis at said locus, wherein the target nucleic acid comprises an mRNA sequence transcribed from a gene coding for a protein selected from the group consisting of c-myb, NMMHC and PCNA.

10. The method of claim 9 wherein the carrier comprises an implantable matrix.

11. The method of claim 9 wherein the carrier comprises a hydrogel.

12. The method of claim 11 wherein the hydrogel comprises a material which is liquid at a temperature below about 37° C.

13. The method of claim 12 wherein the hydrogel material comprises a polyethylene oxide-polypropylene oxide polymer.

14. The method of claim 13 wherein the polymer comprises from about 10 to about 80% by weight polyethylene oxide and from about 20 to about 90% by weight polypropylene oxide.

15. The method of claim 14 wherein the polymer comprises about 70% by weight polyethylene oxide and about 30% by weight polypropylene oxide.

16. The method of claim 9 wherein the oligonucleotide, incorporated within said carrier, is deposited extravascularly.

17. The method of claim 9 wherein said oligonucleotide, incorporated within said carrier, is deposited onto or beneath an adventitial surface of the vascular system.

18. A method for inhibiting restenosis at a vascular tissue locus following injury to the locus, the method comprising:

directly applying to the locus of a vascular tissue injury in vivo an antisense oligonucleotide, complementary to a target nucleic acid expressed in smooth muscle cells and necessary to initiate or support proliferation thereof, the oligonucleotide being applied at a concentration sufficient to permit the oligonucleotide to penetrate smooth muscle cells at the locus, and to induce selective hybridization between said nucleic acid and said antisense oligonucleotide within the smooth muscle cells for a time sufficient to inhibit restenosis at the locus of the vascular tissue injury, wherein the target nucleic acid comprises a portion of an mRNA encoding a protein selected from the group consisting of a c-myb protein, non-muscle myosin heavy chain and PCNA.

19. A method for inhibiting restenosis at a vascular tissue locus following injury to said locus, the method comprising:

directly applying to the locus of a vascular tissue injury in vivo a hydrogel, which is liquid below about 37° C. and gels at body temperature, the hydrogel having incorporated therein an antisense oligonucleotide, complementary to a target nucleic acid expressed in smooth muscle cells and necessary to initiate or support proliferation thereof; and permitting the oligonucleotide present in the hydrogel to diffuse from the hydrogel at a concentration sufficient to permit the oligonucleotide to penetrate smooth muscle cells at the tissue locus and to hybridize with the target nucleic acid for a time sufficient to inhibit restenosis at the locus of the vascular tissue injury, wherein the target nucleic acid comprises a portion of a mRNA encoding a protein selected from the group consisting of a c-myb protein, non-muscle myosin heavy chain and PCNA.

20. The method of claim 19 wherein said hydrogel comprises a polymer of ethylene oxide-propylene oxide repeating units.

\* \* \* \* \*